(12) United States Patent
Fujihara

(10) Patent No.: US 8,299,225 B2
(45) Date of Patent: Oct. 30, 2012

(54) AMIDITE FOR SYNTHESIZING MODIFIED NUCLEIC ACID AND METHOD FOR SYNTHESIZING MODIFIED NUCLEIC ACID

(75) Inventor: Tsuyoshi Fujihara, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 12/902,758

(22) Filed: Oct. 12, 2010

(65) Prior Publication Data

US 2011/0092685 A1    Apr. 21, 2011

Related U.S. Application Data

(62) Division of application No. 12/181,459, filed on Jul. 29, 2008, now Pat. No. 7,910,726.

(30) Foreign Application Priority Data

Sep. 5, 2007   (JP) ................... 2007-230730

(51) Int. Cl.
 C07H 21/04 (2006.01)
 C07H 21/00 (2006.01)
 C07H 19/20 (2006.01)
 C07H 19/10 (2006.01)

(52) U.S. Cl. ............... 536/23.1; 536/25.31; 536/25.34; 536/26.7; 536/26.8

(58) Field of Classification Search ............ None
See application file for complete search history.

(56) References Cited

U.S. PATENT DOCUMENTS

| | | | | | |
|---|---|---|---|---|---|
| 4,500,707 | A | * | 2/1985 | Caruthers et al. | 536/25.34 |
| 4,973,679 | A | * | 11/1990 | Caruthers et al. | 536/26.71 |
| 7,101,986 | B2 | * | 9/2006 | Dellinger et al. | 536/23.1 |
| 7,427,679 | B2 | * | 9/2008 | Dellinger et al. | 536/26.7 |
| 7,910,726 | B2 | * | 3/2011 | Fujihara | 536/26.7 |

FOREIGN PATENT DOCUMENTS

WO   03/078623 A1   9/2003

OTHER PUBLICATIONS

Brown et al., "Modern Machine-aided Methods of Oligodeoxyribonucleotide Synthesis," Chapter 1 in Oligonucleotides and Analogues, A Practical Approach, F. Eckstein (ed.), IRL Press, New York, NY, 1991, only pp. 1-24 supplied.*
Gait et al., "Oligoribonucleotide Synthesis," Chapter 2 in Oligonucleotides and Analogues, A Practical Approach, F. Eckstein (ed.), IRL Press, New York, NY, 1991, only pp. 25-48 supplied.*
Avino, Anna Maria et al.; "Use of NPE-Protecting Groups for the Preparation of Oligonucleotides Without Using Nucleophiles During the Final Deprotection"; Nucleosides & Nuceotides, Dec. 1994, pp. 2059-2069, vol. 13, No. 10.
Eritja, Ramon et al; "A Synthetic Procedure for the Preparation of Oligonucleotides Without Using Ammonia and Its Application for the Synthesis of Olionucleotides Containing O-4-ALKYL Thymidines"; Tetrahedron, Mar. 1992, pp. 4171-4182, vol. 48, No. 20.
Heikkila, Jarmo et al.; "The 9- Fluorenylmethoxycarbonyl (Fmoc) Group for the Protection of Amino Functions of Cytidine, Adenosine, Guanosine and Their 2'-Deoxysugar Derivatives"; Acta Chemica Scandinavica., 1983, pp. 263-265, B37, No. 3.
Koole, Leo H. et al; "Synthesis of Phosphate-Methylated DNA Fragments Using 9-Fluorenylmethoxycarbonyl as Transient Base Protecting Group"; J. Org. Chem., 1989, pp. 1657-1664, vol. 54.
Kuijpers, W.H.A. et al; "The 2-(Acetoxymethyl) Benzoyl (AMB) Group as a New Base-Protecting Group, Designed for the Protection of (Phosphate) Modified Oligonucleotides"; Tetrahedron Letters, 1990, pp. 6729-6732, vol. 31, No. 46.
Kuijpers, W.H.A. et al.; "The application of the AMB protective group in the solid-phase synthesis of methylphosphonate DNA analogues"; Nucleic Acids Research, 1993, pp. 3493-3500, vol. 21, No. 15.

* cited by examiner

Primary Examiner — Lawrence E Crane
(74) Attorney, Agent, or Firm — Westerman, Hattori, Daniels & Adrian, LLP

(57) ABSTRACT

To provide an excellent amidite for synthesizing modified nucleic acid, which enables a protective group therein to be removed under a moderate condition, thereby stably producing a hydroxyl group-containing modified nucleic acid, and a method for synthesizing modified nucleic acid using the amidite. Specifically, an amidite for synthesizing modified nucleic acid, expressed by General Formula (I):

General Formula (I)

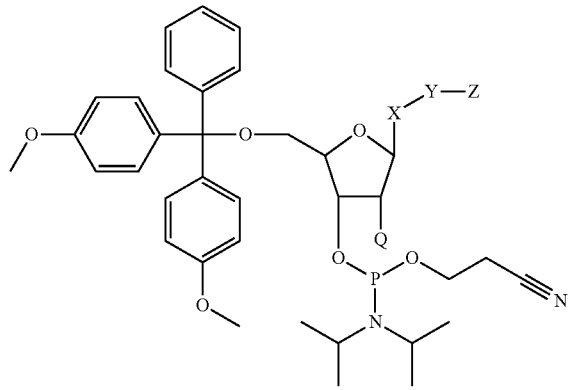

where X represents a base, Y represents a substituent, Z represents a protective group for protecting a hydroxyl group in the substituent, and Q represents one of a hydrogen atom, a hydroxyl group and a hydroxyl group protected by a protective group,
wherein the protective group can be removed in an aprotic solvent, and when the protective group is removed, the hydroxyl group emerges in the substituent, and a method for synthesizing modified nucleic acid using the amidite.

11 Claims, 25 Drawing Sheets

AMIDITE FOR SYNTHESIZING MODIFIED NUCLEIC ACID AND METHOD FOR SYNTHESIZING MODIFIED NUCLEIC ACID

CROSS-REFERENCE TO RELATED APPLICATIONS

This application is a divisional of U.S. application Ser. No. 12/181,459, filed on Jul. 29, 2008 which is based upon and claims the benefits of the priority from the prior Japanese Patent Application No. 2007-230730 filed on Sep. 5, 2007, the entire contents of which are incorporated herein by reference.

BACKGROUND

1. Field of the Invention

The present invention relates to an amidite for synthesizing modified nucleic acid which is preferably used for producing a hydroxyl group-containing modified nucleic acid, and a method for synthesizing modified nucleic acid using the amidite.

2. Description of the Related Art

Unraveling of the whole human genome has shifted the focus of interest of scientists and researchers on the analysis of proteins, which are gene products. It may not be too much to say that substantial protein analysis can be made possible only when a molecule that shows affinity for a protein of interest has been successfully obtained. A cell, however, contains many different types of proteins, and the amino acid sequence and structure of many of which are still unknown.

The most common technique for obtaining a molecule that shows affinity for a specific protein is to prepare an affinity antibody by utilizing the immune system of animal. However, this technique uses animals and requires a large quantity of proteins, a large number of processes and large costs. Additionally, no affinity antibody may be obtained for specific substances with this technique.

A technique called aptamer method (also referred to as SELEX) that does not rely on any living organism has been proposed to avoid this problem. However, while a molecule obtained by this technique strongly interacts with a specific protein, this technique is not applicable to all proteins. In view of the above-identified circumstances, the inventors proposed a modified aptamer method that is established by improving the aptamer method so as to use modified nucleic acid (see International Publication No. WO2003/078623).

Solid-phase synthesis of nucleic acids was initiated as long ago as more than 20 years, and automatic synthesizers were already sold then. Solid-phase synthesis of nucleic acid is carried out, for example by making a nucleic acid material (amidite) combine in a condensation reaction with a solid carrier (e.g. CPG) in which a nucleoside is immobilized; this condensation reaction needs to take place, with only a phosphoric acid portion in the amidite and a hydroxyl group in another amidite being involved in the condensation reaction, and other reactive groups not being involved in the condensation reaction. Therefore, it is necessary to prevent an exocyclic amino group, etc. contained in a base of an amidite used from being involved in the condensation reaction by introducing a protective group, and to eliminate (remove) the protective group after the condensation reaction has finished completely. Conventionally, benzoyl group, isobutyryl group and the like have been used for protective groups introduced into exocyclic amino groups in bases, and a method of allowing concentrated ammonia water to act at 55° C. for 8 hours to 15 hours so as to remove these protective groups has been common.

However, when a modified nucleic acid that shows affinity for a protein as described above is produced under the above-described conventional deprotection conditions, a modified moiety in the modified nucleic acid (a substituent showing affinity for a protein) is removed together with a protective group. Thus, modified nucleic acids can not be stably produced. Therefore, when the modified nucleic acids are to be produced, amidites which enable protective groups therein to be removed under more moderate conditions are desired to avoid removal of substituents which show affinity for a protein together with protective groups.

For example, in the related art, nucleic acid amidites which enable protective groups therein to be removed by diazabicycloundecene (DBU) that is a bulky base (refer to Acta Chem, Scand., B37, 263 (1983) and J. Org. Chem., 54, 1657 (1989)) have been reported. However, they are not suitable for practical use, since the amidites for synthesizing nucleic acid represented are unstable in acetonitrile that is an aprotic solvent (refer to Tetrahedron Letters 46, 6729 (1990)). Additionally, although it has also been reported that amidites for synthesizing nucleic acid enable protective groups therein to be removed in pyridine under a condition of 0.5M DBU for 16 hours (refer to Tetrahedron 40, 4171 (1992) and Nucleodied & Nuclrotides 13, 2059 (1994)), they are problematic in that nucleic acid bases are alkylated owing to highly-concentrated DBU and deprotection for a long period of time. In addition, although it has also been reported that amidites for synthesizing nucleic acid represented enable protective groups therein to be removed using $K_2CO_3$ in methanol (refer to Tetrahedron Letters 46, 6729 (1990) and Nucleic Acids Research 21, 3493 (1993)), they are problematic in that esters, etc. decompose because $K_2CO_3$ that is a base is used in methanol that is a protic solvent.

Thus, as things stand at present, development of an excellent amidite for synthesizing modified nucleic acid which enables a protective group therein to be removed under a moderate condition, thereby stably producing modified nucleic acid that can be suitably used for analysis of a target substance such as a protein, and of a method for synthesizing modified nucleic acid using the amidite for synthesizing modified nucleic acid is still hoped for.

SUMMARY

According to an aspect of an embodiment, there provides an amidite for synthesizing modified nucleic acid, expressed by General Formula (I):

General Formula (I)

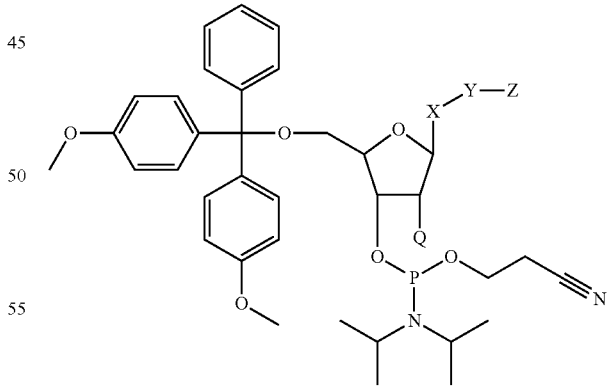

where X represents a base, Y represents, a substituent, Z represents a protective group for protecting a hydroxyl group in the substituent, and Q represents one of a hydrogen atom, a hydroxyl group and a hydroxyl group protected by a protective group, wherein the protective group can be removed in an aprotic solvent, and when the protective group is removed, the hydroxyl group emerges in the substituent.

Figure 1:
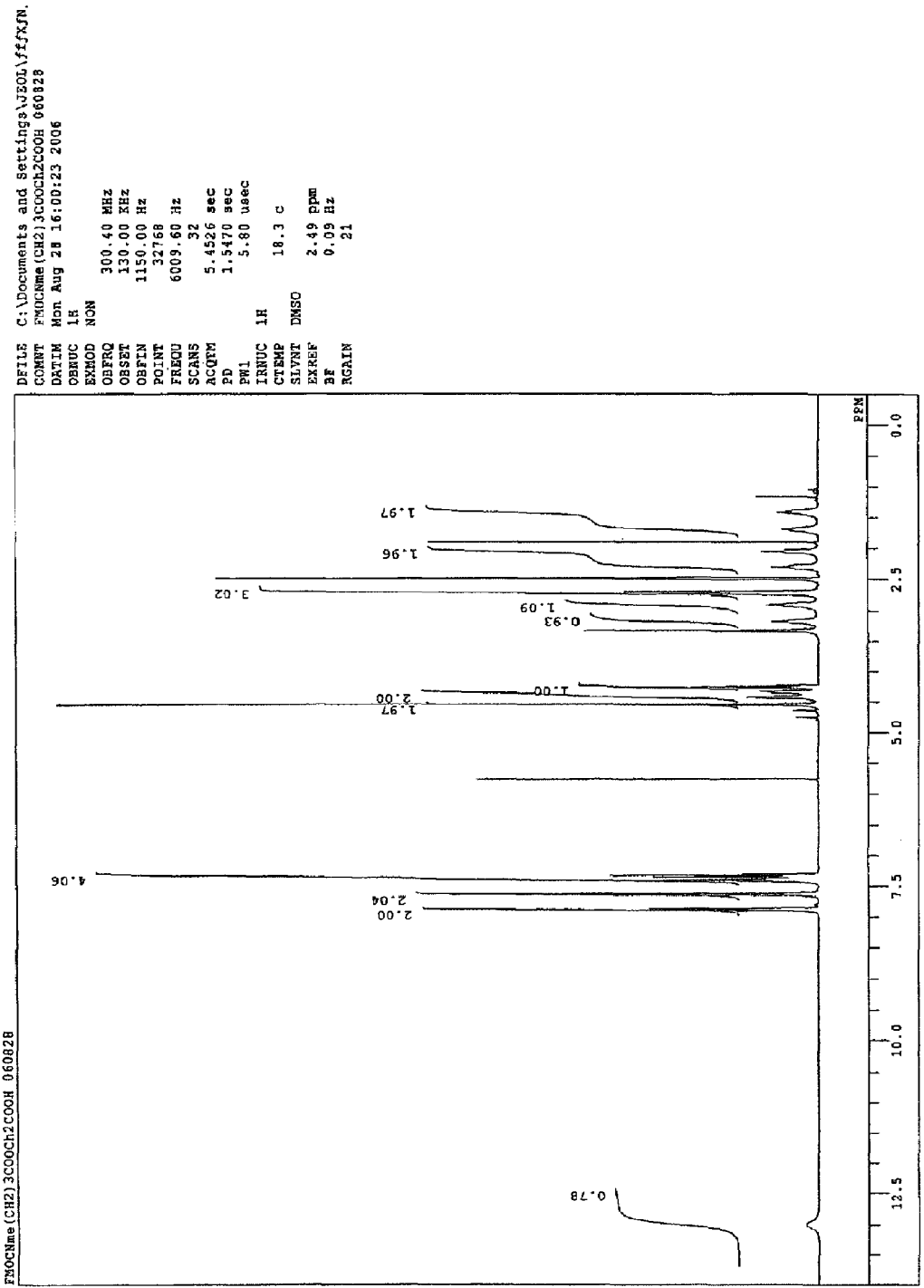
FIG. 1 is a $^1$-NMR spectrum of compound II in Example 1.
Figure 2:
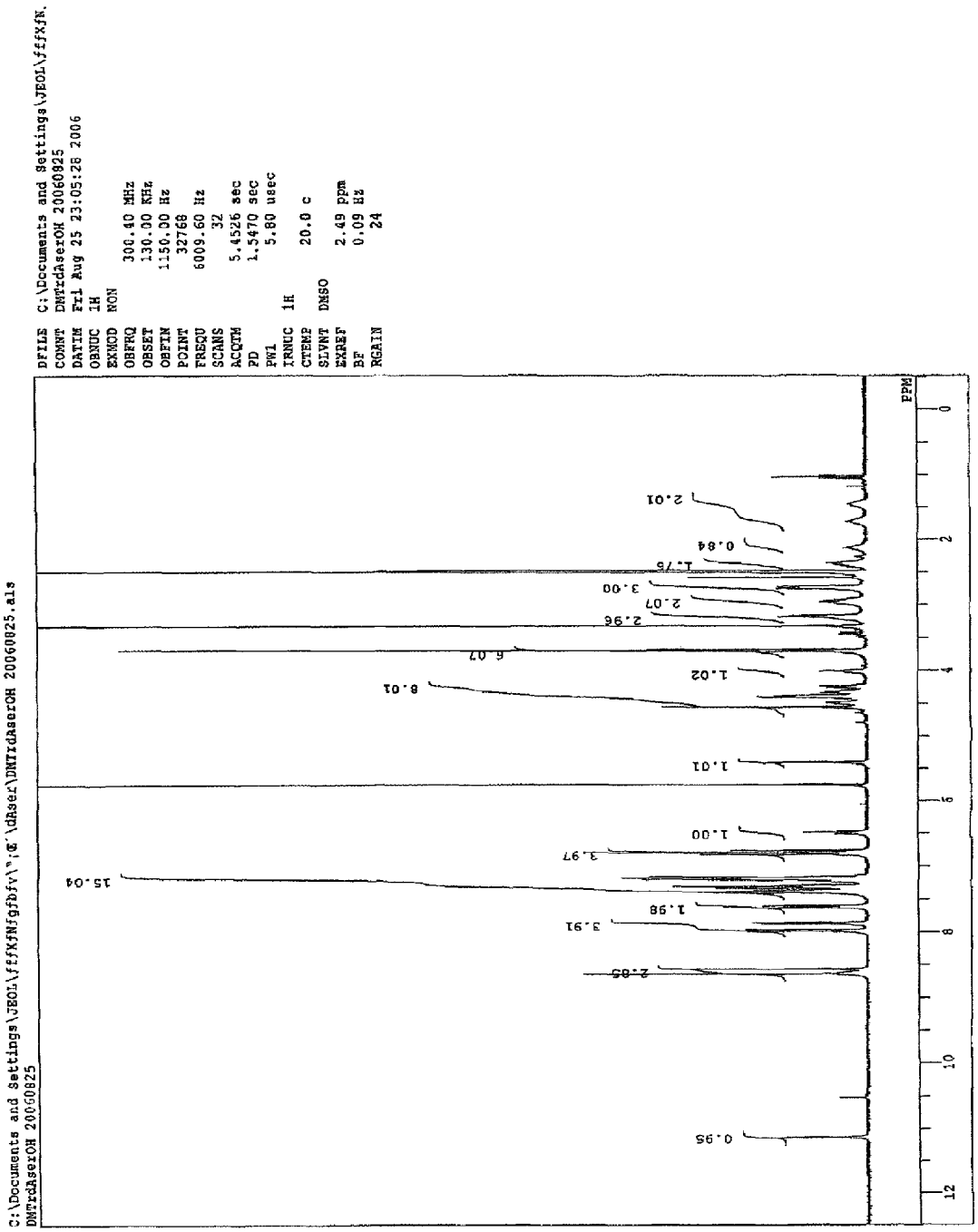
FIG. 2 is a $^1$H-NMR spectrum of compound IV$_S$ in Example 1.
Figure 3:
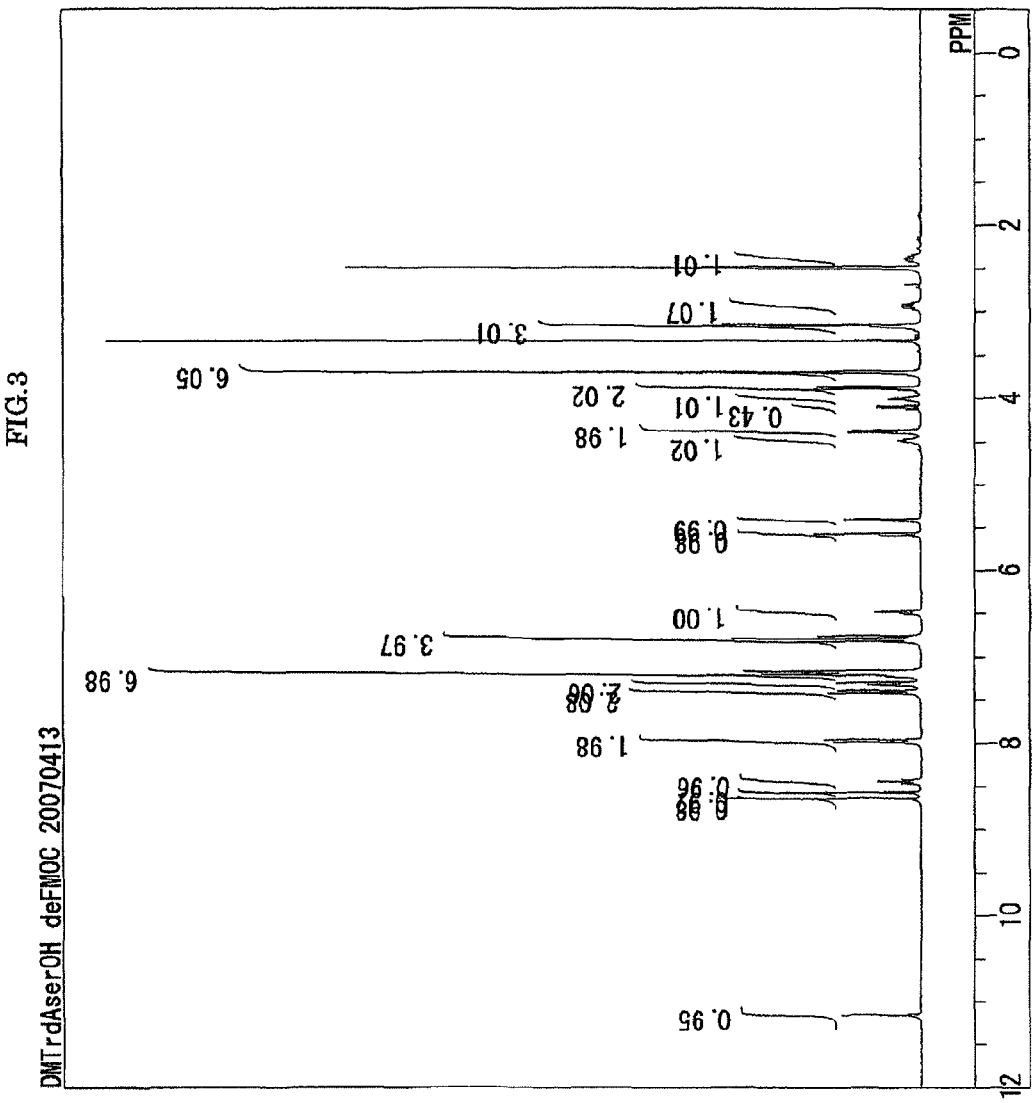
FIG. 3 is a $^1$H-NMR spectrum of compound IV$_{S'}$ in Example 1.
Figure 4A:
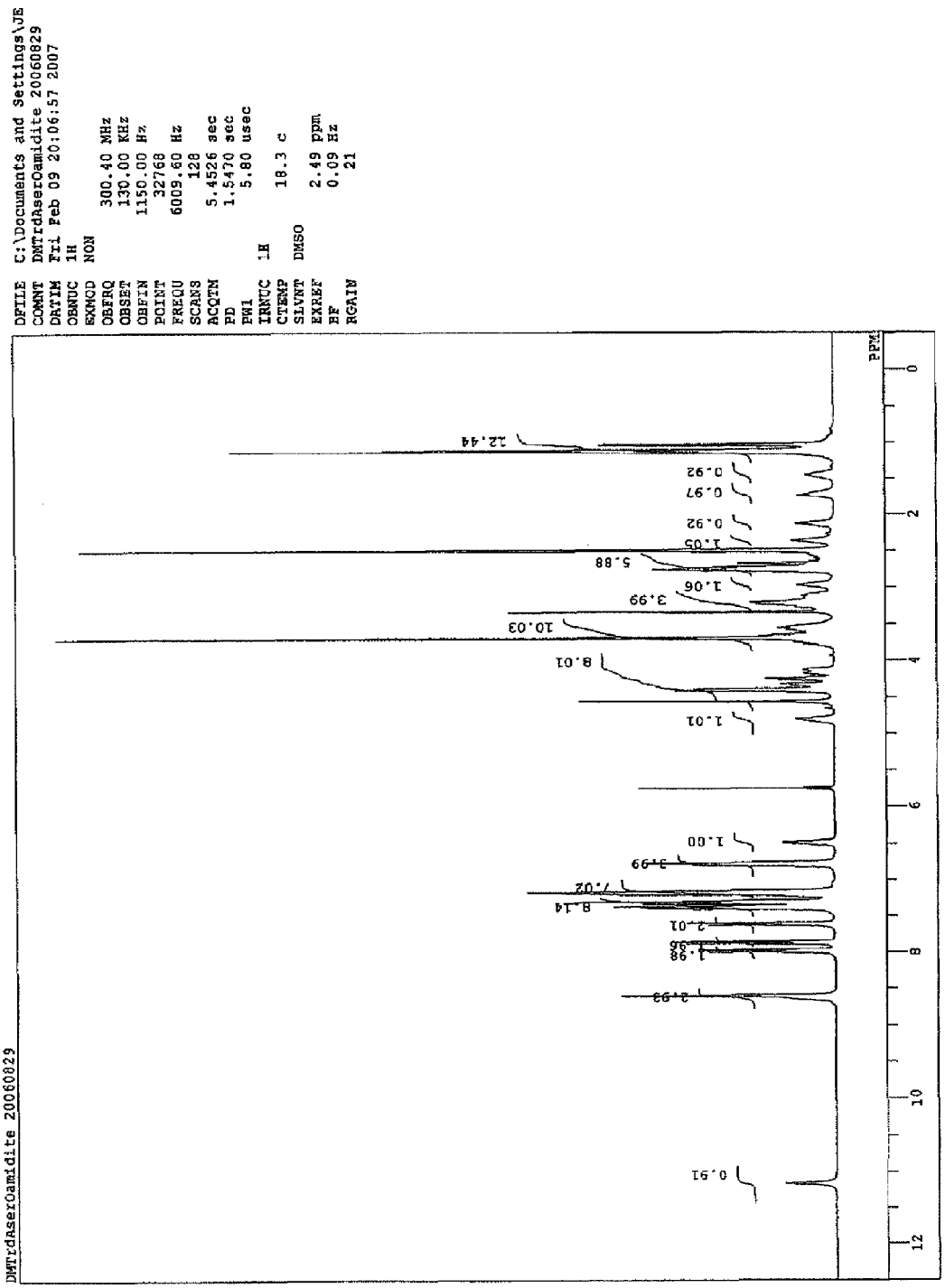
FIG. 4A is a $^1$H-NMR spectrum of compound V$_S$ in Example 1.
Figure 4B:
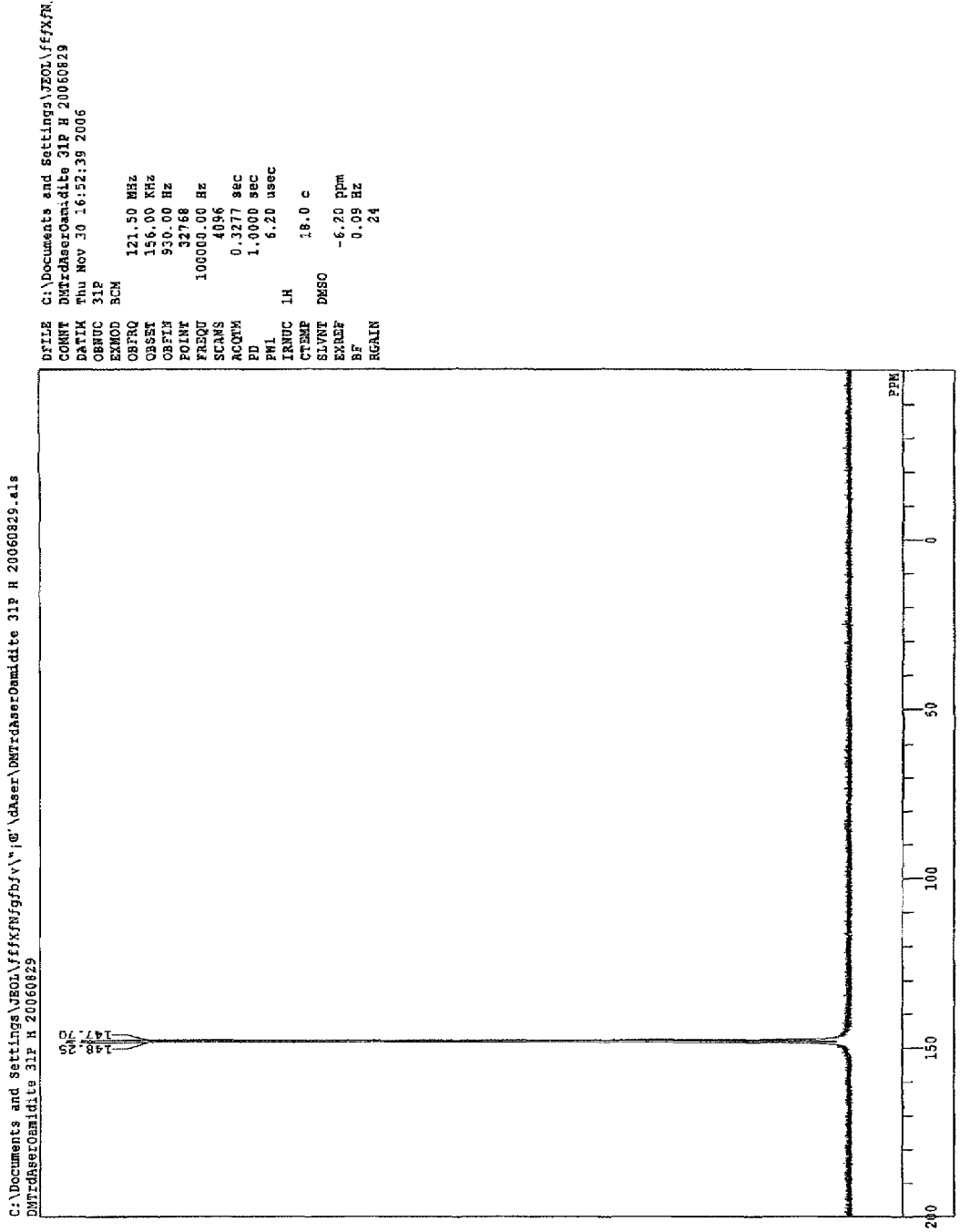
FIG. 4B is a $^{31}$P-NMR spectrum of compound V$_S$ in Example 1.
Figure 5:
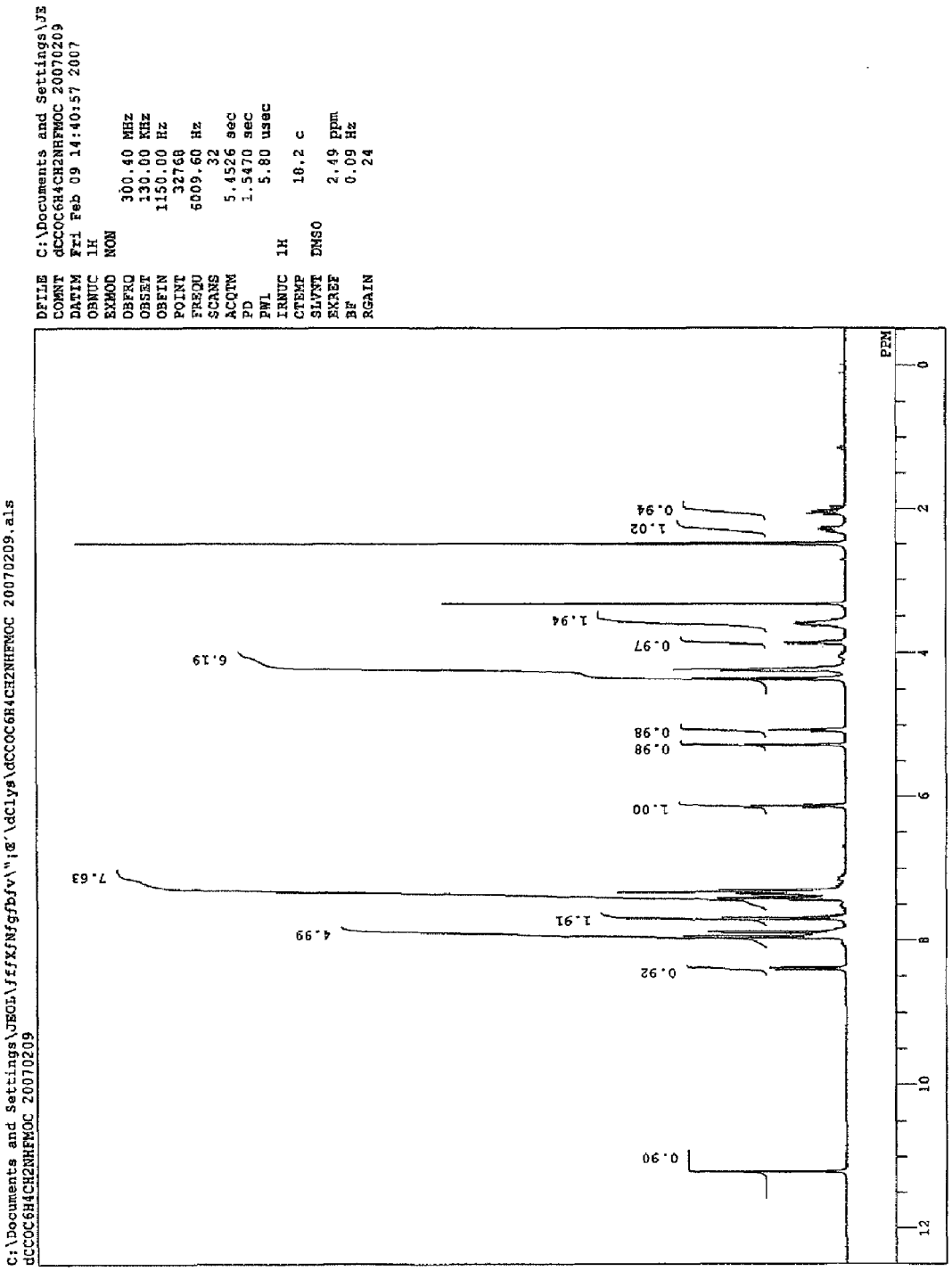
FIG. 5 is a $^1$H-NMR spectrum of compound X in Example 1.
Figure 6:
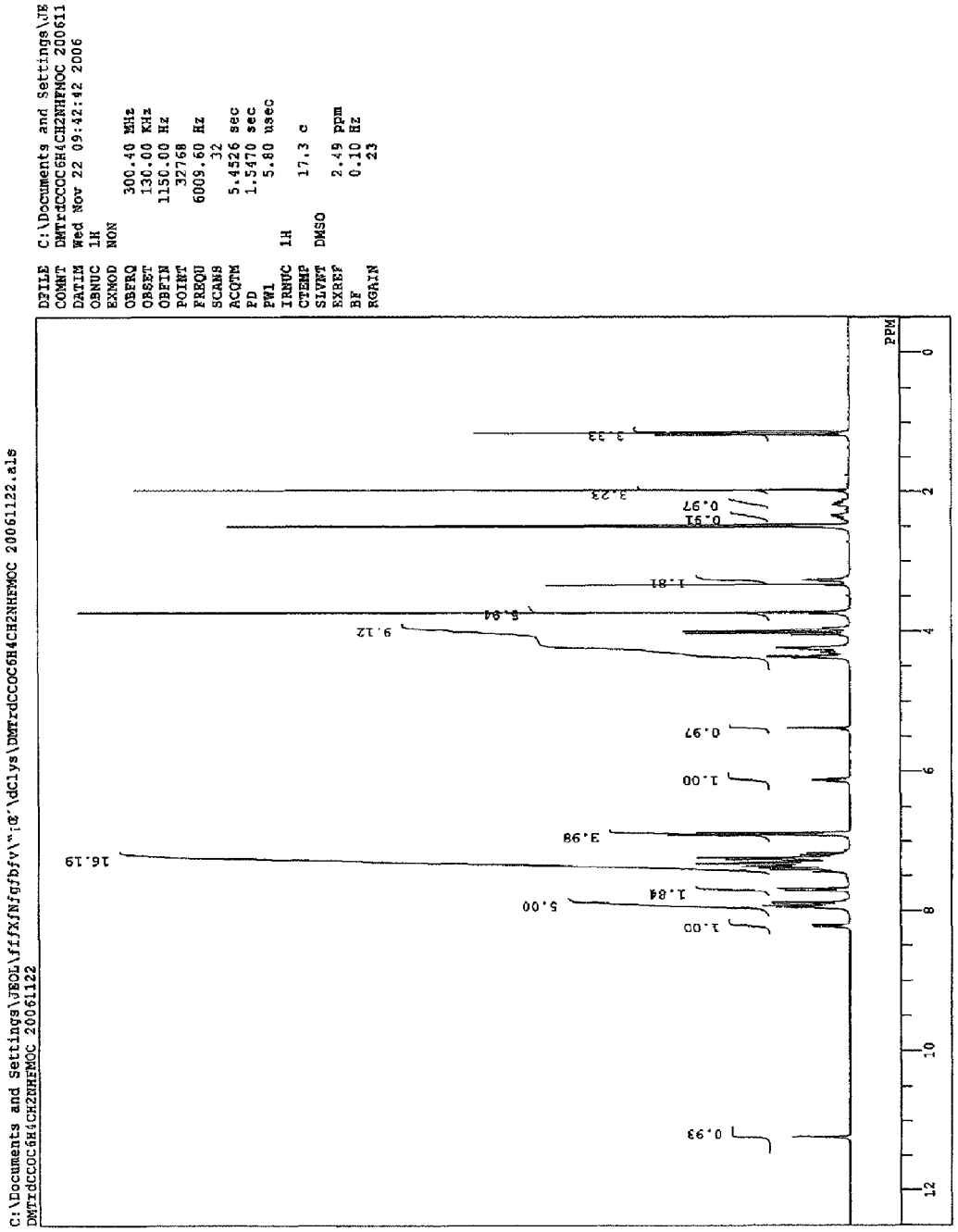
FIG. 6 is a $^1$H-NMR spectrum of compound IIIc in Example 1.
Figure 7:
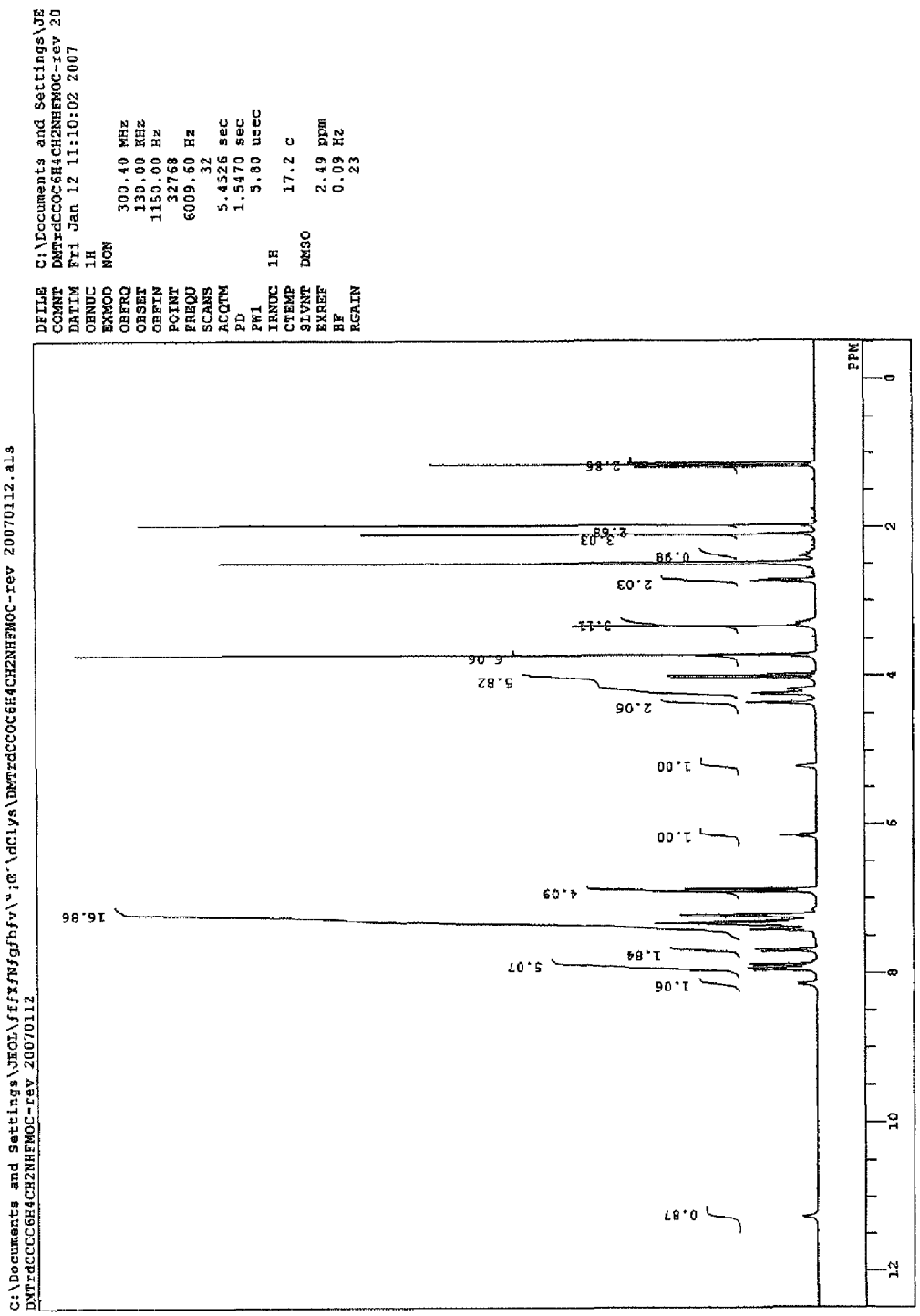
FIG. 7 is a $^1$H-NMR spectrum of compound XI in Example 1.
Figure 8:
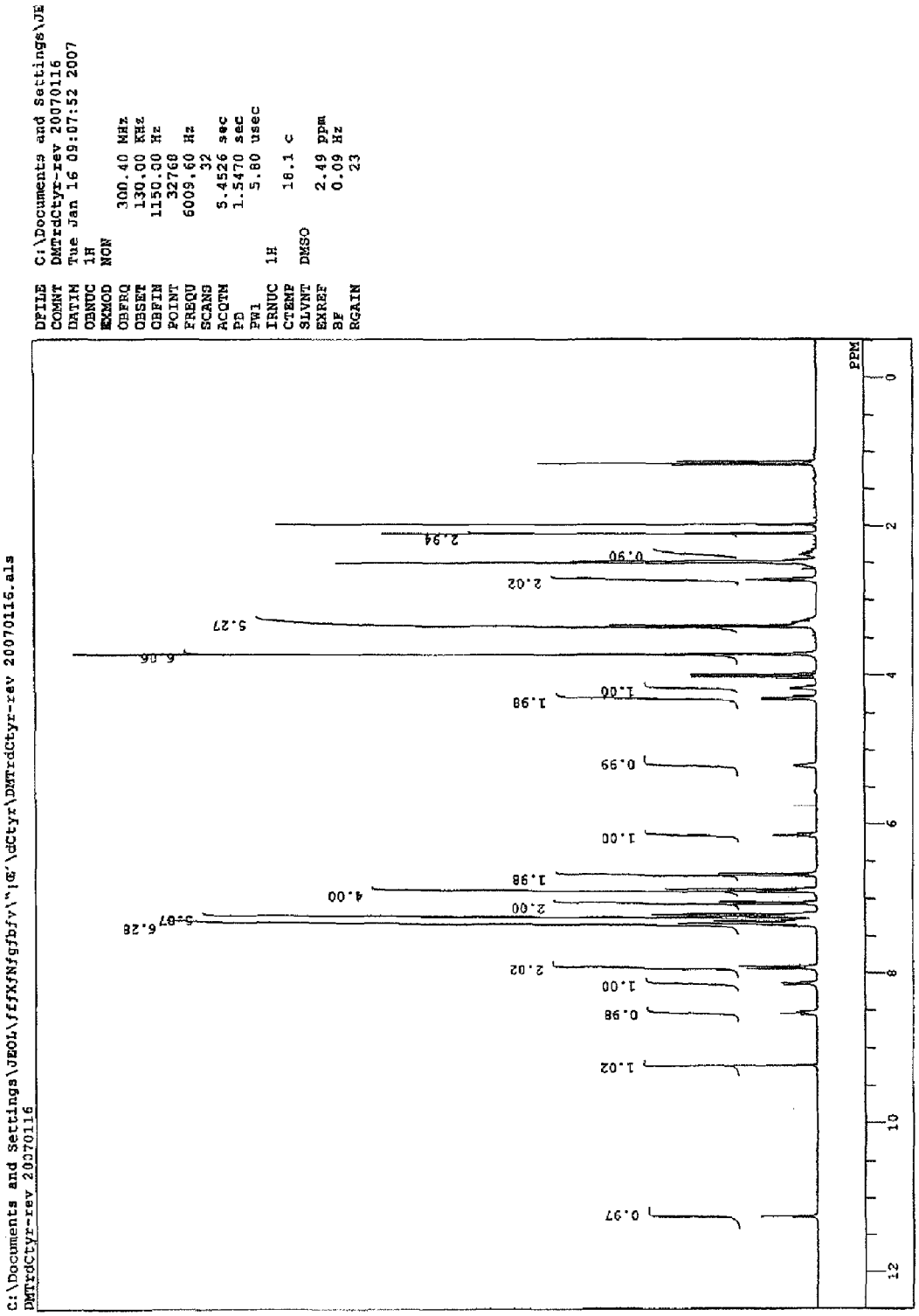
FIG. 8 is a $^1$H-NMR spectrum of compound XII$_Y$ in Example 1.
Figure 9:
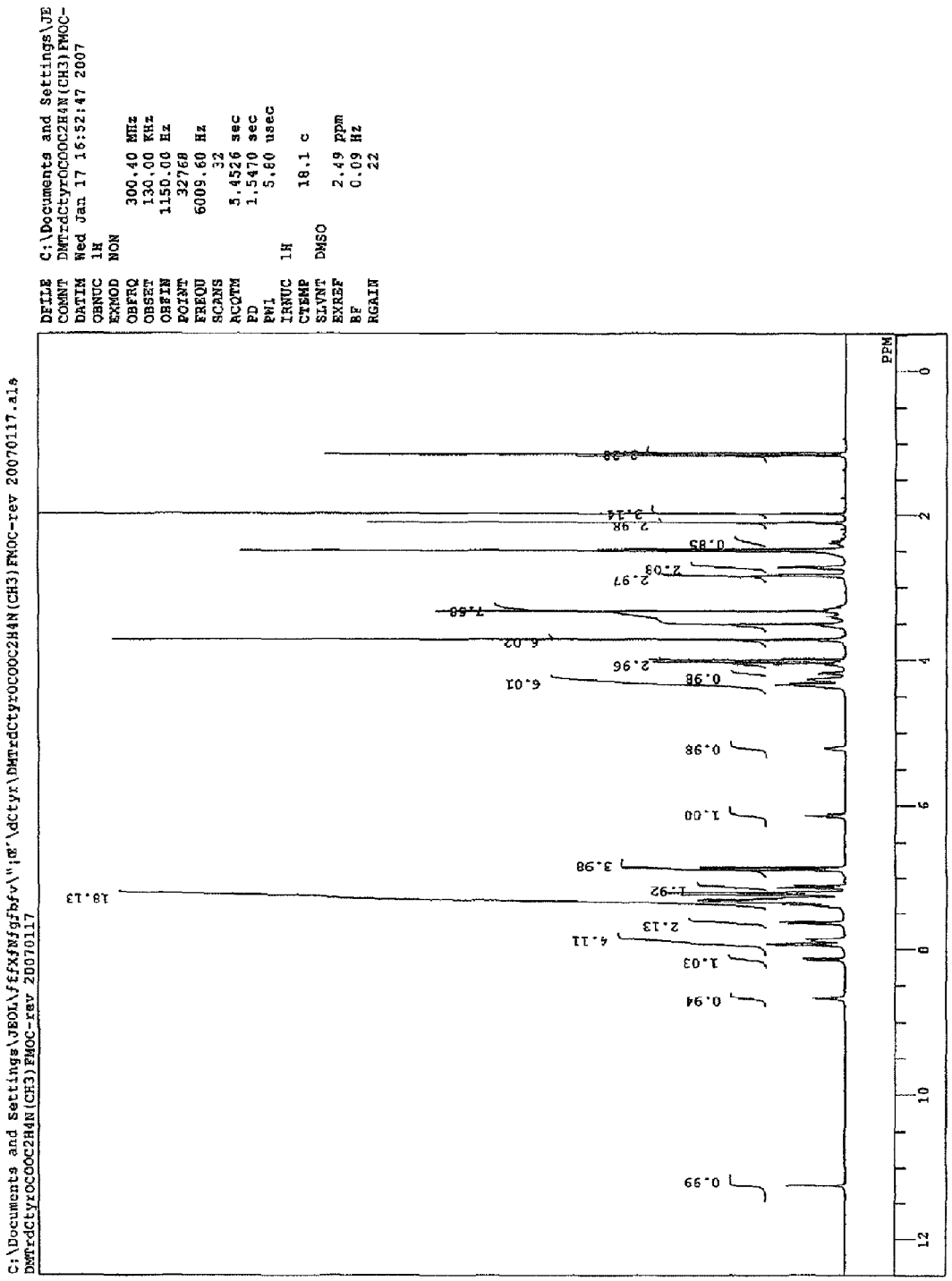
FIG. 9 is a $^1$H-NMR spectrum of compound XIV$_Y$ in Example 1.
Figure 10:
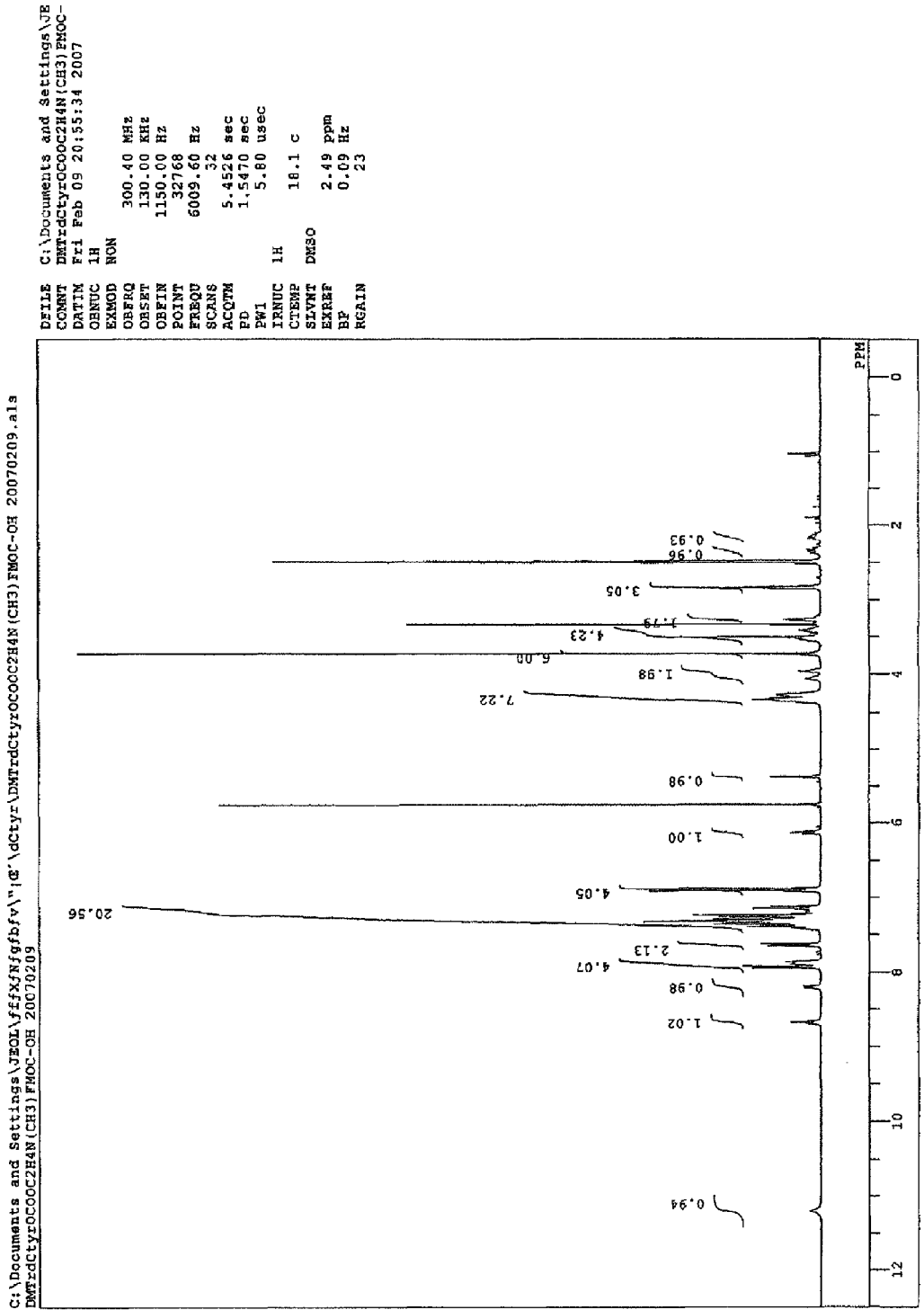
FIG. 10 is a $^1$H-NMR spectrum of compound IV$_Y$ in Example 1.
Figure 11A:
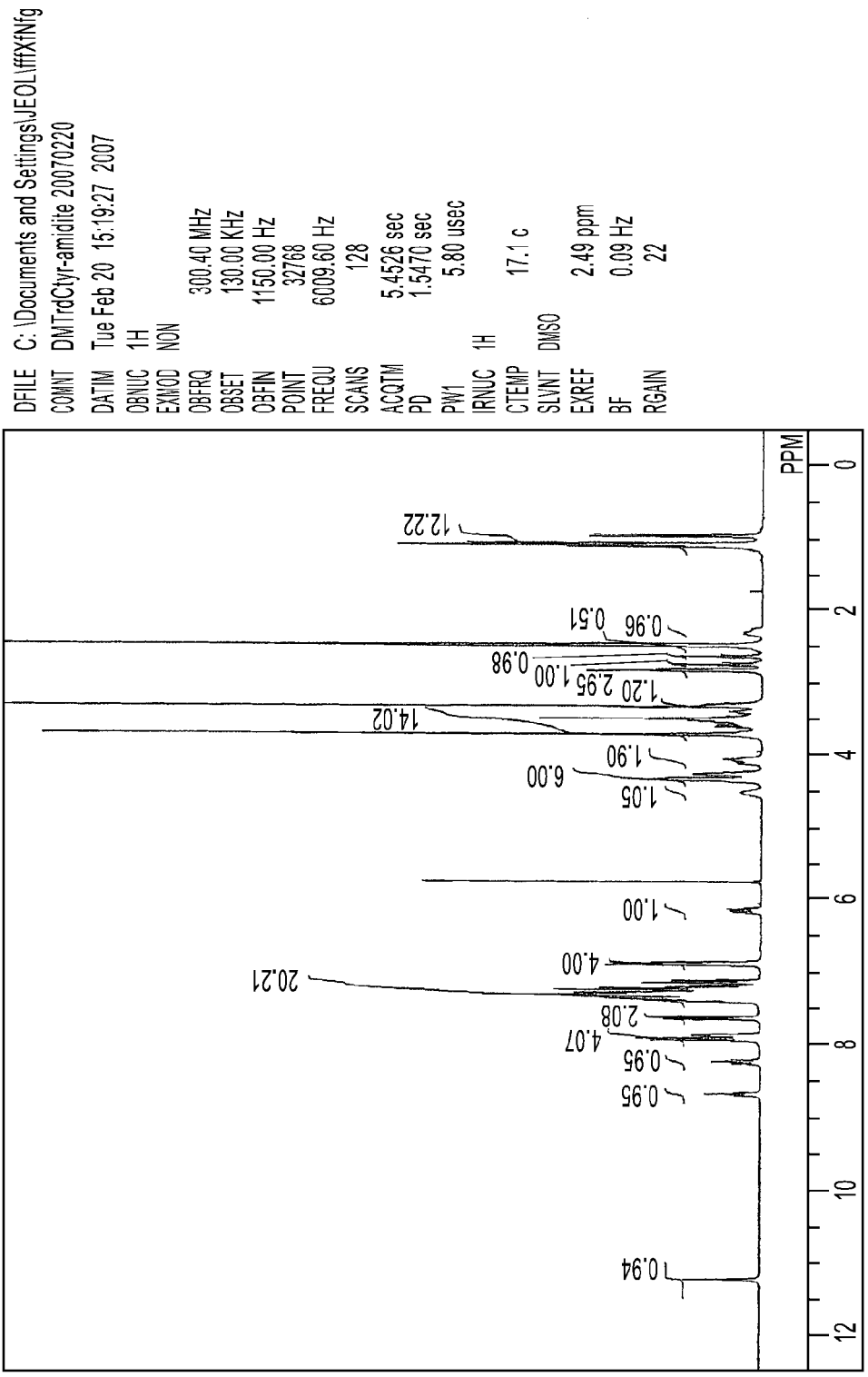
FIG. 11A is a $^1$H-NMR spectrum of compound V$_{Tyr}$ in Example 1.
Figure 11B:
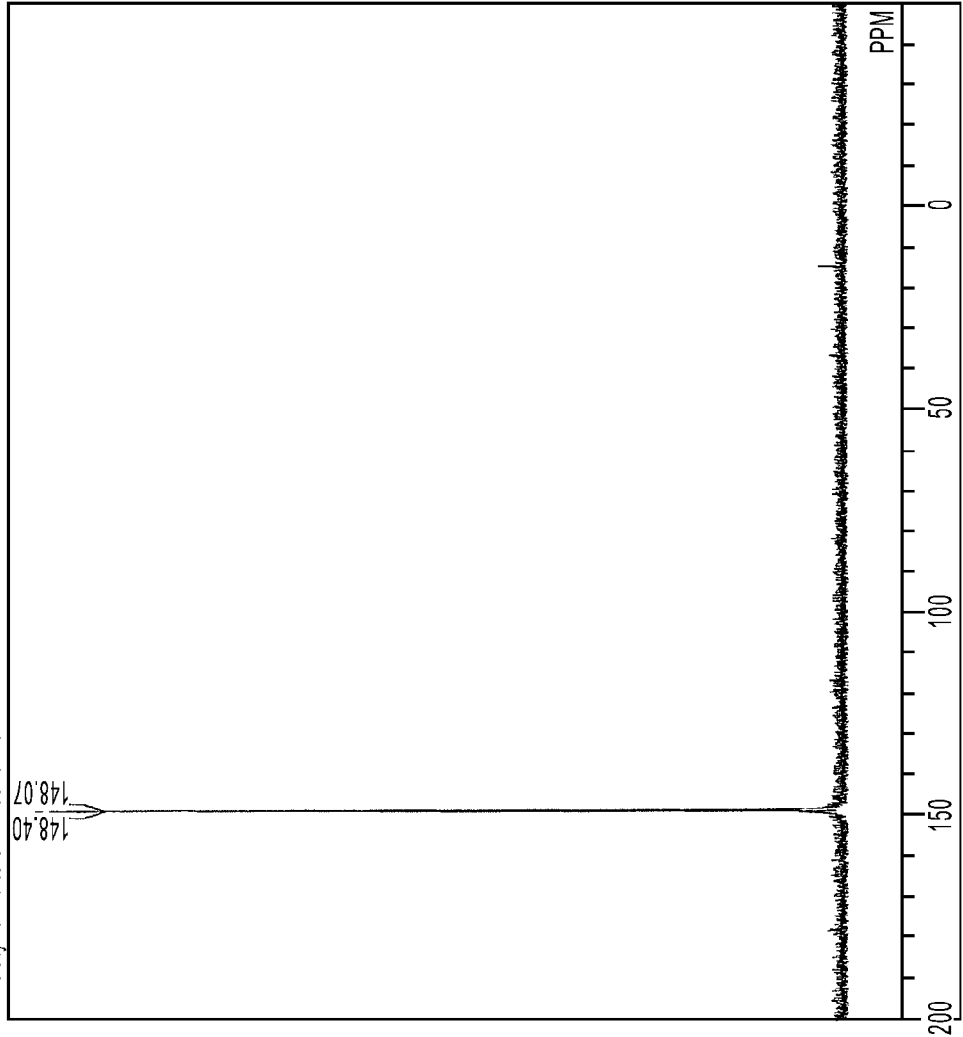
FIG. 11B is a $^{31}$P-NMR spectrum of compound V$_Y$ in Example 1.
Figure 11C:
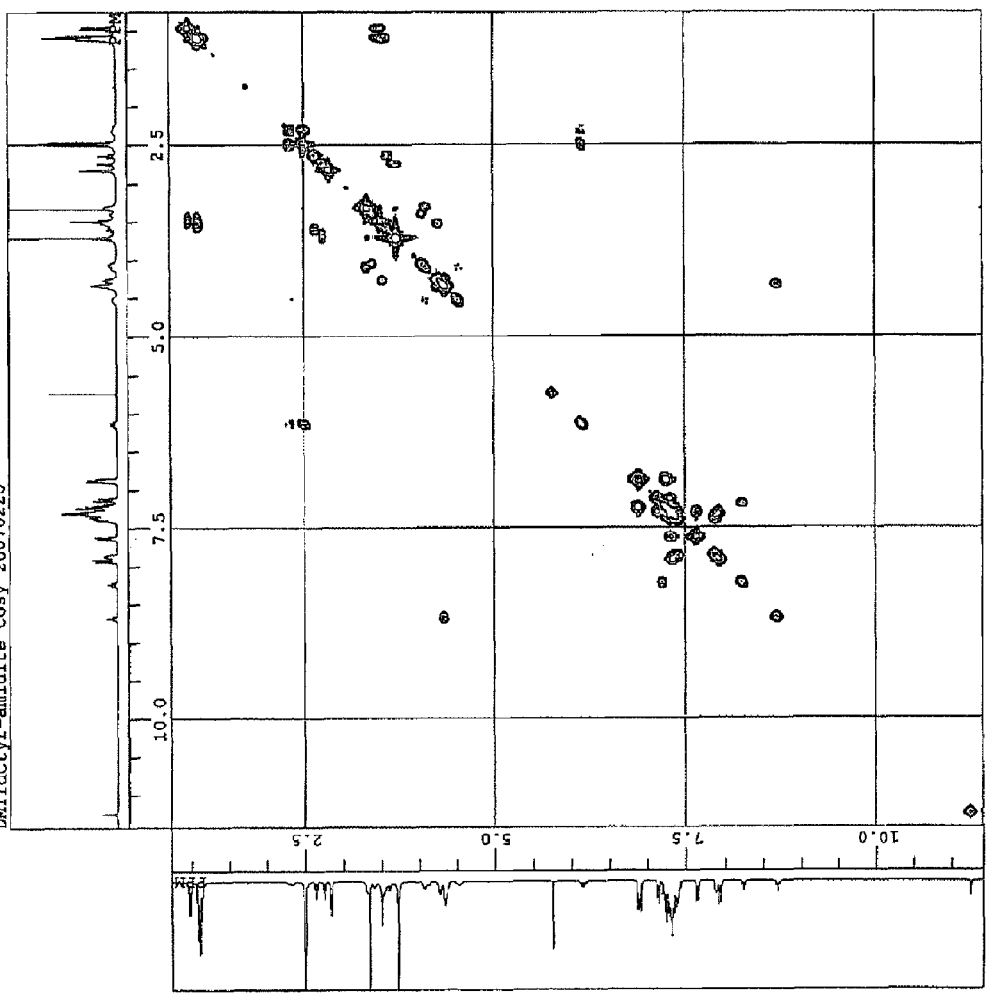
FIG. 11C is a HHcosy spectrum of compound V$_Y$ in Example 1.

DETAILED DESCRIPTION OF THE EMBODIMENTS (Amidite for Synthesizing Modified Nucleic Acid)

An amidite for synthesizing modified nucleic acid is expressed by General Formula (I), in which a protective group can be removed in an aprotic solvent and a hydroxyl group emerges in a substituent when the protective group is removed.

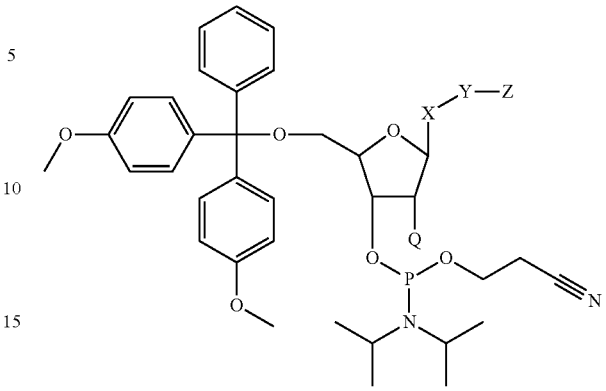

General Formula (I)

where X represents a base, Y represents a substituent, Z represents a protective group for protecting a hydroxyl group in the substituent, and Q represents one of a hydrogen atom, a hydroxyl group and a hydroxyl group protected by a protective group.

<Protective Group for Protecting Hydroxyl Group in Substituent>

In General Formula (I), the protective group represented by Z is a protective group for protecting a hydroxyl group in the substituent. The protective group is not particularly limited and may be suitably selected according to the purpose, as long as it can be removed in an aprotic solvent, that is, a protective group can be removed under a moderate condition.

"A protective group can be removed under a moderate condition" means that, for example, a protective group can be removed by a bulky base in an aprotic solvent. The aprotic solvent is not particularly limited, and may be suitably selected according to the purpose. Examples thereof include acetonitrile, dichloromethane, DMF (N,N-dimethylformamide) and N-methylpyrrolidone. The bulky base is not particularly limited, and may be suitably selected according to the purpose. Examples thereof include DBU (1,8-diazabicyclo[5.4.0]-7-undecene), DBN (1,5-diazabicyclo[4.3.0]-5-nonene) and tetramethylguanidine. Of these, it is preferable that the protective group be removed by DBU in acetonitrile. Additionally, in this case, it is preferable that the concentration of DBU required to remove the protective group be 0.5M or less, more preferably 0.1M or less and still more preferably 0.01M or less. It is desirable that the time required for removal be 8 hours or less, more preferably 1 hour or less, and still more preferably 15 minutes or less.

The protective group is preferably formed of any one of a 3-aminopropionic acid derivative, 4-aminobutyric acid derivative, 5-aminovaleric acid derivative, aminomethyl carbonate derivative, aminoethyl carbonate derivative, amino benzoic acid derivative, aminomethyl benzoic acid derivative, aminoethyl benzoic acid derivative, aminophenylacetic acid derivative, aminomethyl phenylacetic acid derivative, aminophenyl propionic acid derivative, and aminomethyl phenyl propionic acid derivative.

Specific examples of the protective groups include protective groups expressed by General Formulae (II) to (III).

General Formula (II)

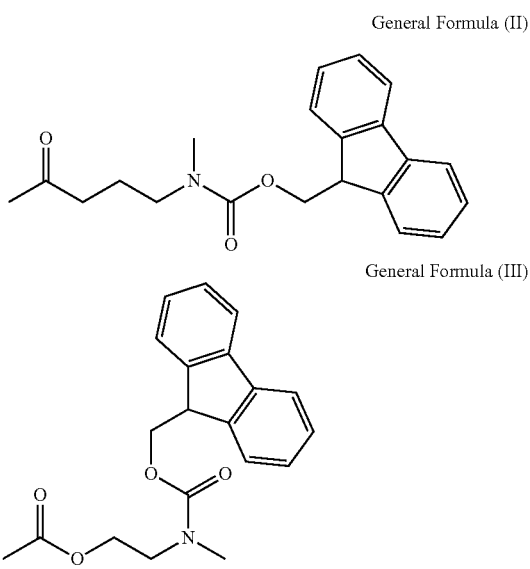

General Formula (III)

<Substituent>

In General Formula (I), the substituent represented by Y is not particularly limited and may be suitably selected according to the purpose, as long as a hydroxyl group emerges in the substituent (a hydroxyl group is exposed on a surface of the substituent) when the protective group is removed. Examples of the substituents include naturally occurring amino acids and non-naturally occurring amino acids, metal complexes, fluorescent dyes, oxidation-reduction dyes, spin-labeling bodies, a hydrogen atom, alkyl groups having 1 to 10 carbon atoms and groups expressed by formulae (1) to (10) shown below.

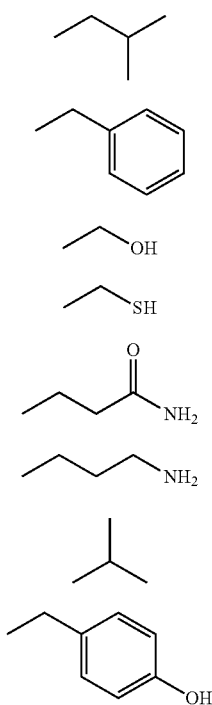

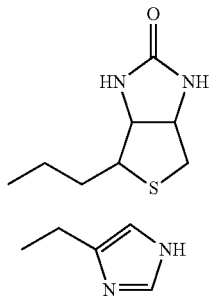

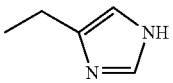

Naturally occurring and non-naturally occurring amino acids are not particularly limited and may be suitably selected according to the purpose. Examples thereof include valine, leucine, isoleucine, alanine, arginine, glutamine, lysine, asparagic acid, glutamic acid, proline, cysteine, threonine, methionine, histidine, phenylalanine, tyrosine, tryptophan, asparagine, glycine and serine.

Metal complexes are not particularly limited and may be suitably selected according to the purpose, as long as ligands are coordinated to metal ions. Examples thereof include Ru bipyridyl complexes, ferrocene complexes and nickel imidazole complexes.

Fluorescent dyes are not particularly limited and may be suitably selected according to the purpose. Examples thereof include fluoroscein dyes, rhodamine dyes, eosin dyes and NBD dyes.

Oxidation-reduction dyes are not particularly limited and may be suitably selected according to the purpose. Examples thereof include leuco dyes such as leucoaniline and leucoanthocyanin.

Spin labeling bodies are not particularly limited and may be suitably selected according to the purpose. Examples thereof include iron N-(dithiocarboxy)sarcosine and TEMPO (tetramethylpiperidine) derivatives.

Alkyl groups having 1 to 10 carbon atoms are not particularly limited and may be suitably selected according to the purpose. Examples thereof include a methyl group, ethyl group, propyl group, isopropyl group, butyl group, isobutyl group, tert-butyl group, pentyl group, neopentyl group, hexyl group, cyclohexyl group, octyl group, nonyl group and decyl group.

Any of these substituents may be substituted further.

<Base>

The base represented by X in General Formula (I) is not particularly limited and may be suitably selected according to the purpose. Examples thereof include adenine (A), guanine (G), cytosine (C), thymine (T) and uracil (U). The position where the substituent is introduced to the base is not particularly limited and may be suitably selected according to the purpose, although the sixth position of adenine base, the sixth position of cytosine base and the second position of guanine base are preferable. In this case, the substituent is necessary to be introduced in the base in order not to be removed together when the protective group is removed under a moderate condition.

<Hydrogen Atom, Hydroxyl Group or Hydroxyl Group Protected by Protective Group>

In General Formula (I), Q represents one of a hydrogen atom, a hydroxyl group and a hydroxyl group protected by a protective group. The protective groups for protecting the hydroxyl groups are not particularly limited and may be suitably selected according to the purpose. Examples thereof include the protective groups shown below.

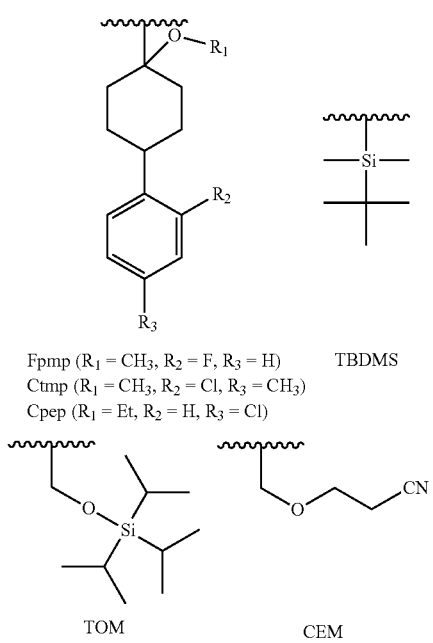

Fpmp (R₁ = CH₃, R₂ = F, R₃ = H)
Ctmp (R₁ = CH₃, R₂ = Cl, R₃ = CH₃)
Cpep (R₁ = Et, R₂ = H, R₃ = Cl)

TBDMS

TOM  CEM

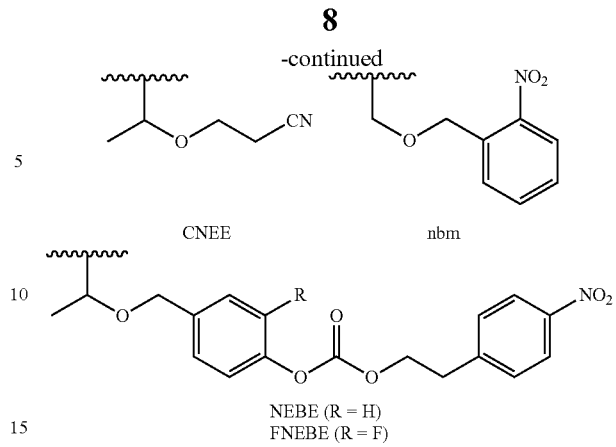

CNEE  nbm

NEBE (R = H)
FNEBE (R = F)

The protective group in the hydroxyl group is preferably a protective group which can be removed in an aprotic solvent, that is, a protective group which can be removed under a moderate condition. Here, "a protective group can be removed under a moderate condition" means as described in <Protective Group for Protecting Hydroxyl Group in Substituent>.

<Specific Examples of Amidite for Synthesizing Modified Nucleic Acid>

Specific examples of the amidite for synthesizing modified nucleic acid include, but not limited to, those expressed by Structural Formulae (1) to (2) shown below.

Structural Formula (1)

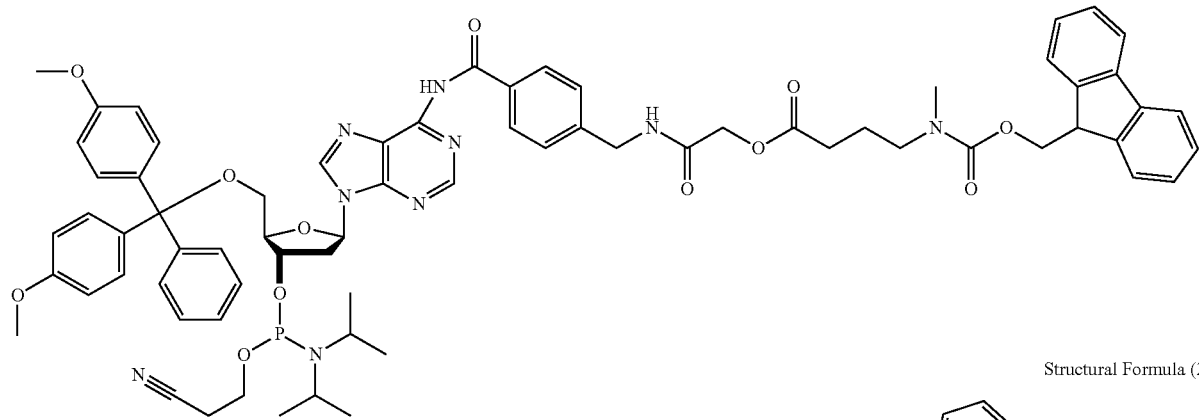

Structural Formula (2)

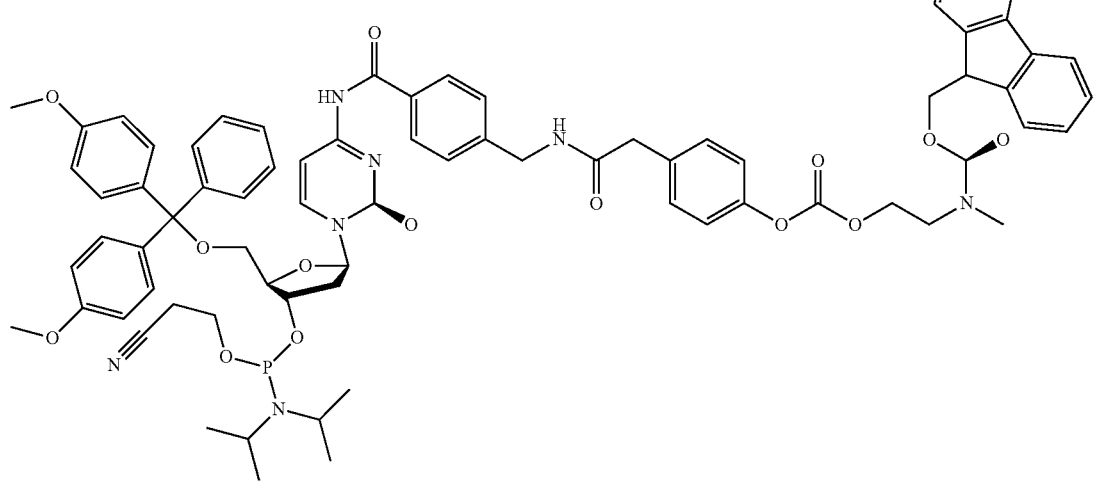

A method for synthesizing the amidite for synthesizing modified nucleic acid is not particularly limited and may be suitably selected according to the purpose. The amidite can be synthesized by, for example, a method described in Examples later.

(Method for Synthesizing Modified Nucleic Acid)

A method for synthesizing modified nucleic acid uses the amidite for synthesizing modified nucleic acid.

The method for synthesizing modified nucleic acid is not particularly limited and may be suitably selected according to the purpose, as long as the amidite for synthesizing modified nucleic acid is used. Examples thereof include a conventional method for synthesizing nucleic acid, in which a solid-phase method is combined with a diester method, a triester method, a phosphite method, a phosphoramidite method, an H-phosphonate method and a thiophosphite method. Also, the method for synthesizing modified nucleic acid can be conducted using a conventional automatic nucleic acid synthesizer, for example.

In the method for synthesizing modified nucleic acid, the amidite(s) for synthesizing modified nucleic acid may be used alone or in combination. As the amidite for synthesizing modified nucleic acid (nucleic acid source), the amidites for synthesizing modified nucleic acid may be used alone or may be used in combination with other amidites. In this case, as other amidites, amidites which enable protective groups therein to be removed under moderate conditions as described above are preferably used; for example an amidite for synthesizing nucleic acid which is disclosed in Japanese Patent Application No. 2007-000576 can be used.

In the method for synthesizing the modified nucleic acid, the amidite for synthesizing modified nucleic acid (and/or other amidites) is subjected to a condensation reaction, and then a protective group in the amidite for synthesizing modified nucleic acid (and/or other amidites) is removed. Conditions of the deprotection (removal of protective group) are not particularly limited, and may be suitably selected according to the purpose. The protective group is preferably removed under the moderate condition as described above; for example, it is preferred that the protective group be removed by a bulky base in an aprotic solvent. The aprotic solvent and the bulky base are the same as those described above. Also, the concentration and the time required for the deprotection are the same as those described above.

Because the protective group is removed under a moderate condition, the substituent in the amidite for synthesizing modified nucleic acid is not removed. A hydroxyl group, which has not emerged in the substituent before the protective group is removed, emerges in the substituent (exposed on a surface of the substituent) by removing the protective group.

(Modified Nucleic Acid)

A modified nucleic acid is obtained by the method of synthesizing modified nucleic acid. That is, the modified nucleic acid contains a modified nucleotide unit having a substituent in which a hydroxyl group partially emerges (or a hydroxyl group is exposed on a surface thereof).

The number of nucleotide units that form the modified nucleic acid is not particularly limited and may be suitably selected according to the purpose. However, the number of nucleotide units is preferably 10 to 200, more preferably 20 to 100, and still more preferably 30 to 80. In the modified nucleotide units forming the modified nucleic acid, the proportion of the modified nucleotide unit derived from the amidite (a modified nucleotide unit having a substituent, in which a hydroxyl group emerges (or a hydroxyl group is exposed on a surface thereof)) is not particularly limited and may be suitably selected according to the purpose. The modified nucleic acid may have either a DNA sequence or a RNA sequence, which may be single strand or double stranded.

Because the modified nucleic acid has a substituent in which a hydroxyl group emerges (or a hydroxyl group is exposed on a surface thereof), it can be bonded to a target substance such as a protein via the hydroxyl group. Therefore, the modified nucleic acid can be preferably used for analysis of a target substance such as a protein.

EXAMPLES

Hereinafter, Examples of the present invention will be described, which however shall not be construed as limiting the scope of the present invention.

Example 1

Synthesis of Amidite for Synthesizing Modified Nucleic Acid

Amidites $V_S$, $V_Y$ for synthesizing modified nucleic acid were synthesized as described below. Note that amidites $V_S$, $V_Y$ respectively correspond to amidites expressed by Structural Formulae (1) and (2) shown above.

Compounds I and III$_A$ were synthesized according to a synthesis method disclosed in Japanese Patent Application No. 2007-69378.

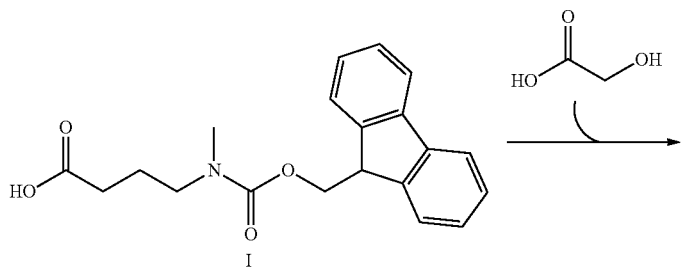

-continued
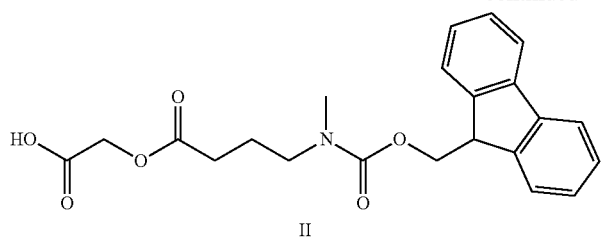
II
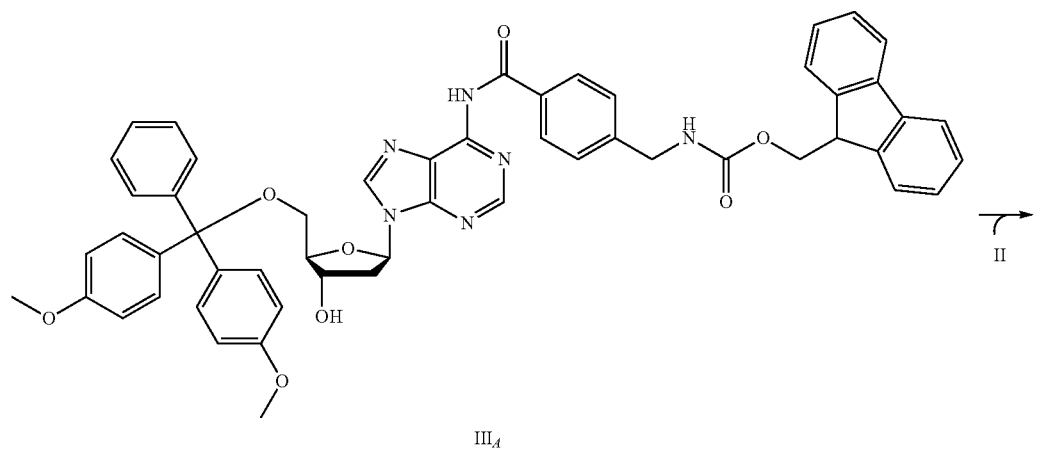
III_A
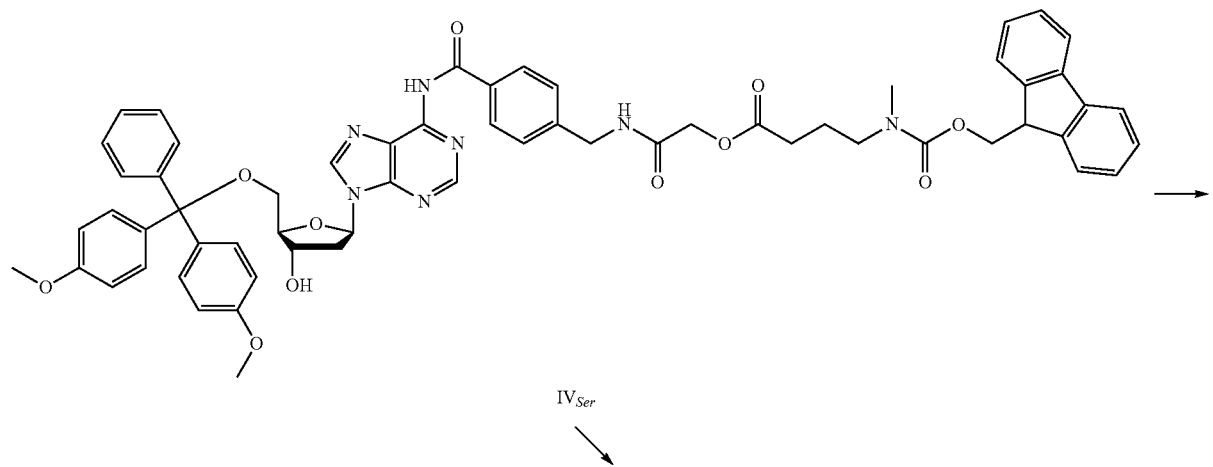
IV_Ser
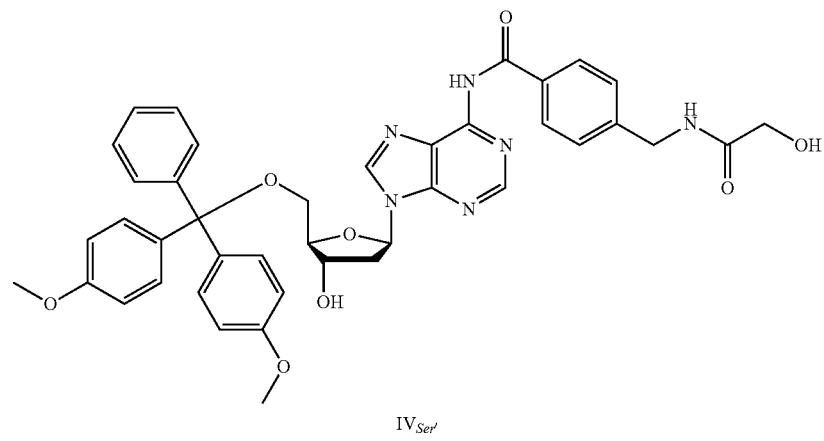
IV_Ser'

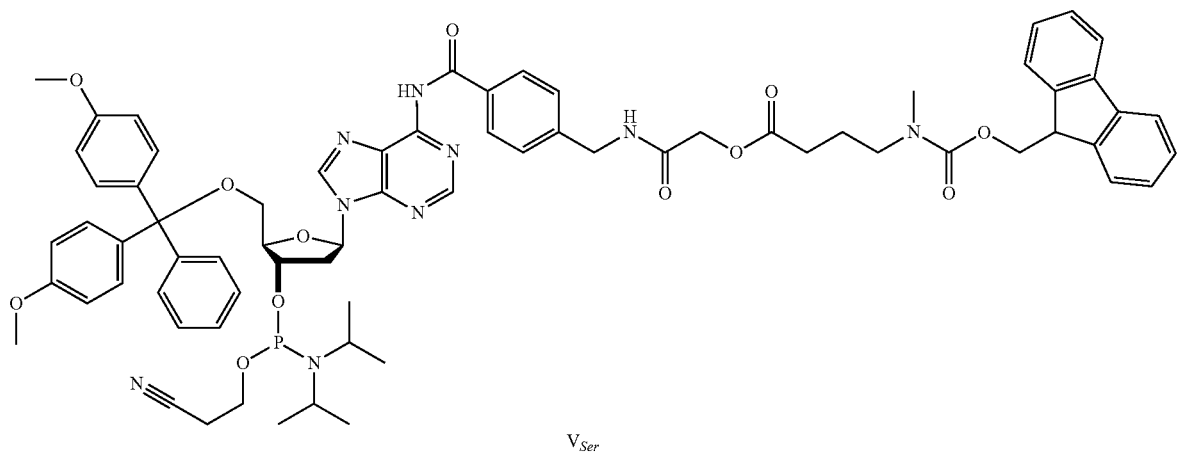

$V_{Ser}$

<Synthesis of II>

In dehydrated acetonitrile, 13.58 g (40 mmol) of I was dissolved and concentrated under reduced pressure. The dissolvation and concentration under reduced pressure was repeated three times. In 200 mL of dehydrated acetonitrile, the obtained residue was dissolved, and 3.88 mL (48 mmol) of pyridine and 6.79 g (40 mmol) of silver nitrate were added, and then 4.93 mL (40 mmol) of pivaloyl chloride was added under an ice-cooled condition and stirred for 15 minutes at 0° C. Subsequently, 4.56 g (60 mmol) of glycolic acid was further added thereto and stirred for 4 hours at room temperature. The reaction solution was diluted with dichloromethane, and washed with water. The dichloromethane solution was concentrated under reduced pressure and the obtained residue was purified by medium pressure chromatography (1% acetic acid, dichloromethane:ethanol=100:0→19:1) to obtain 13.03 g (82%) of a target product II.

<Synthesis of $IV_S$>

In 20 mL of dehydrated dichloromethane, 10.58 g (10 mmol) of $III_A$ was dissolved, 2.40 mL (15 mmol) of triethylsilane and 2.24 mL (15 mmol) of diazabicycloundecene were added and stirred for 10 minutes at room temperature. In the reaction mixture, a mixed solution of 1.27 mL (16.5 mmol) of trifluoroacetic acid, 1.45 mL (18 mmol) of pyridine and 10 mL of dichloromethane were added to obtain a reaction mixture A.

In dehydrated toluene, 4.97 g (12.5 mmol) of II was dissolved, and concentrated under reduced pressure. The dissolvation and concentration under reduced pressure was repeated three times. In 30 mL of dehydrated dichloromethane, the obtained residue was dissolved, 1.58 g (13.8 mmol) of N-hydroxysuccinic acid imide was added, and then 2.71 g (13.1 mmol) of dicyclohexylcarbodiimide was added in an ice-cooled condition and stirred for 1 hour at room temperature. Undissolved substances were removed by filtration and a filtrate was added to the reaction mixture A. The reaction mixture was then stirred for 1 hour at room temperature. Subsequently, 5 mL of methanol was added thereto, and stirred for 30 minutes. The reaction solution was diluted with dichloromethane and washed with water. The dichloromethane solution was concentrated under reduced pressure and the obtained residue was purified by medium pressure chromatography (dichloromethane:ethanol 97:3→47:3) to obtain 10.11 g (95%) of a target product $IV_S$.

<Synthesis of $V_S$>

In dehydrated acetonitrile and dehydrated dichloromethane, 10.11 g (9.48 mmol) of $IV_S$ was dissolved, and concentrated under reduced pressure. The dissolvation and concentration under reduced pressure was repeated three times. In 38 mL of dehydrated dichloromethane, the obtained residue was dissolved, and 57.9 mg (0.47 mmol) of dimethylaminopyridine and 1.87 mL (11.4 mmol) of diisopropylethylamine were added under an ice-cooled condition. Then, 9.5 mL of a methylene chloride solution of 2.33 mL (10.4 mmol) of 2-cyanoethyl diisopropylchlorophosphoroamidite was added dropwise over 5 minutes or more. The mixed solution was stirred for 1 hour at 0° C. Subsequently, 9.5 mL of methanol was added to the mixed solution and stirred for 30 minutes. The reaction solution was diluted with dichloromethane and washed with water. The dichloromethane solution was concentrated under reduced pressure and the obtained residue was purified by medium pressure chromatography (2% pyridine in ethyl acetate; hexane=2:1-2% pyridine, 3% ethanol in ethyl acetate 1:0→0:1) to obtain 10.31 g (86%) of a target product $V_S$.

<Synthesis of $IV_{S'}$>

In 2.5 mL of dichloromethane, 533 mg (0.5 mmol) of $IV_{S'}$ was dissolved, and 0.12 mL (0.75 mmol) of triethylsilane and 0.11 mL (0.75 mmol) of DBU were added and stirred for 30 minutes at room temperature. The reaction mixture was directly purified by column chromatography (8%→16% ethanol in dichloromethane) to obtain 347 mg (93.2%) of $IV_{S''}$.

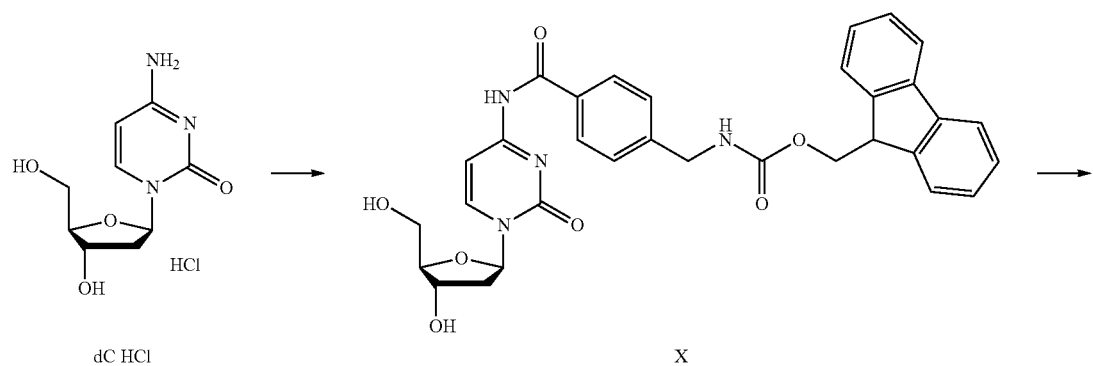
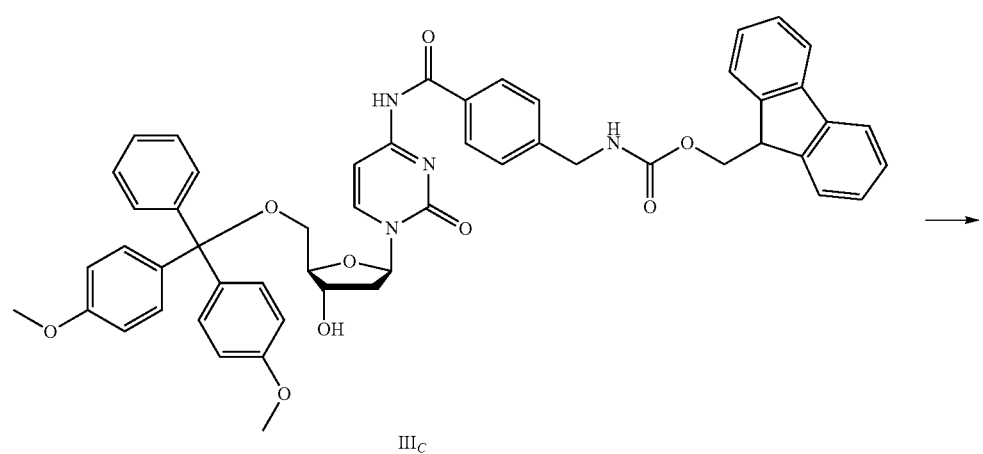
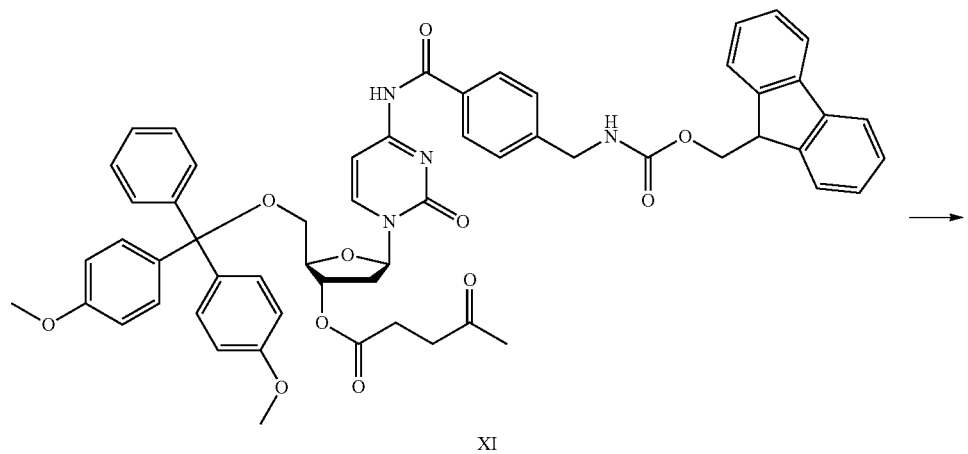

-continued
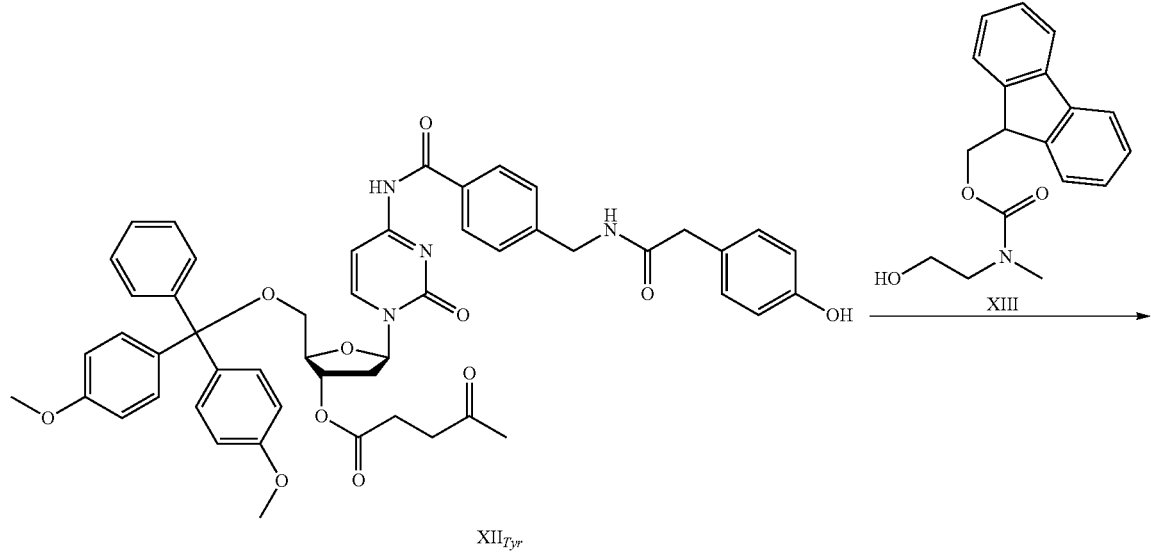
XII_Tyr
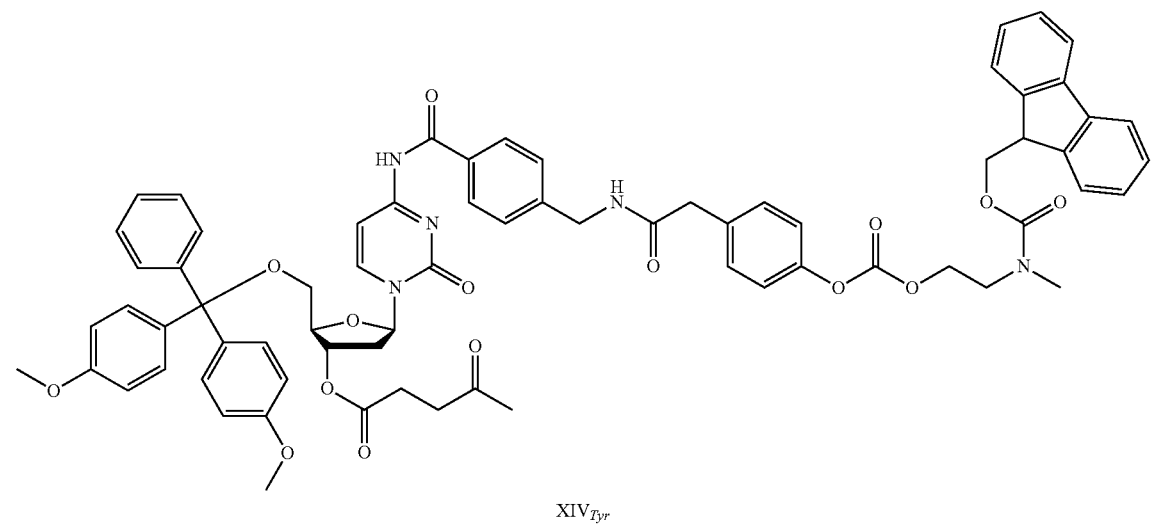
XIV_Tyr
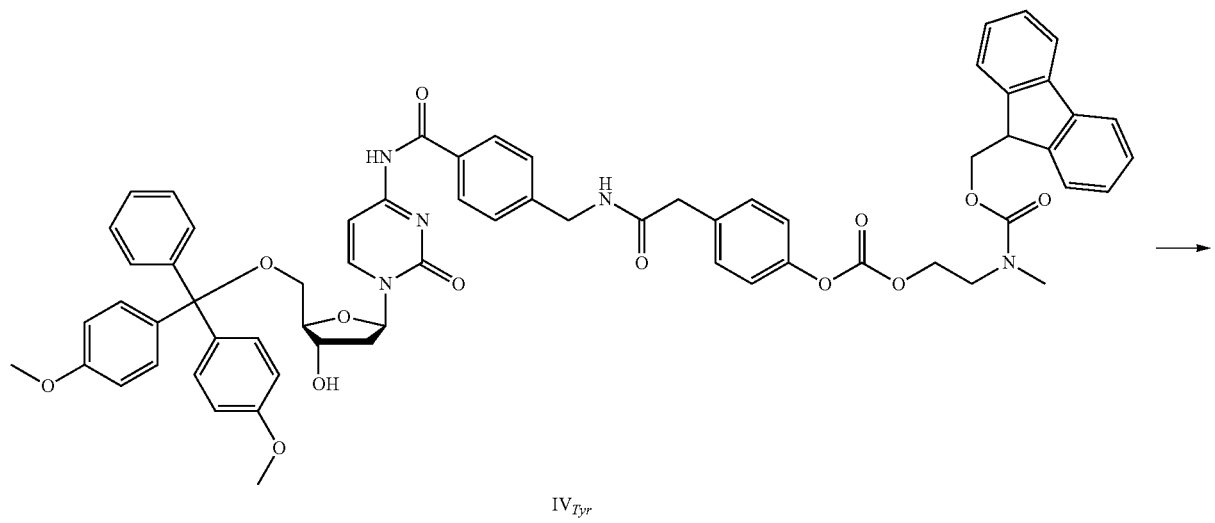
IV_Tyr

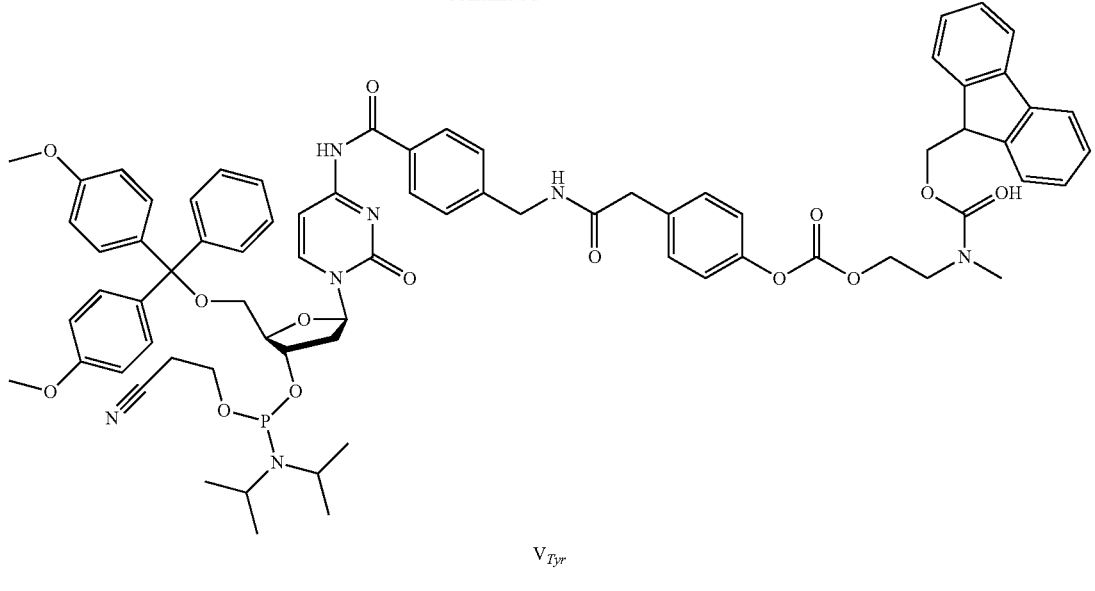

$V_{Tyr}$

<Synthesis of X>

In 400 mL of dehydrated dichloromethane, 37.3 g (100 mmol) of 4-(FMOC-aminomethyl)benzoic acid was suspended, and 12.9 mL (150 mmol) of oxaryl chloride and 0.15 mL (1.9 mmol) of dimethylformamide were added in an argon atmosphere and stirred for 7 hours at room temperature. The reaction solution was concentrated under reduced pressure. The obtained residue was added to dehydrated toluene, and concentrated under reduced pressure, and then dissolved in 400 mL of dehydrated dichloromethane to obtain a solution A.

In dehydrated pyridine, 29.0 g (110 mmol) of deoxycytidine hydrochloride was suspended, and concentrated under reduced pressure. The suspension and concentration under reduced pressure was repeated three times. The obtained residue was suspended with 375 mL of dehydrated pyridine, 46.4 mL (396 mmol) of trimethylchlorosilane was added thereto at 0° C., and stirred for 1 hour at room temperature, subsequently cooled to 0° C. again. Then, the solution was introduced to the solution A under an ice-cooled condition. The reaction mixture was stirred for 1 hour at room temperature. Under an ice-cooled condition, 100 mL of water was added to the reaction mixture and stirred for 8 hours at room temperature. The solution was concentrated under reduced pressure. To the obtained residue, 500 mL of ethyl acetate and 500 mL of water were added, sufficiently stirred and then filtrated to obtain 61.6 g of a crude target product X.

<Synthesis of IIIc>

In dehydrated pyridine, 61.6 g of the crude target product X was dissolved, and concentrated under reduced pressure. The dissolvation and concentration under reduced pressure was repeated three times. In 500 mL of dehydrated pyridine, the obtained residue was dissolved, and 33.92 g (100 mmol) of 4,4'-dimethoxytritylchloride was added under an ice-cooled condition, and then stirred for 8 hours at 0° C. Subsequently, 20 mL of methanol was added thereto and stirred for 30 minutes. The solution was concentrated under reduced pressure, diluted with ethyl acetate, and then washed with water. The ethyl acetate solution was concentrated under reduced pressure, and then the obtained residue was purified by medium pressure chromatography (ethylacetate:ethanol=1: 0→19:1) to obtain 76.2 g of a target product IIIc (90%, 2 steps).

<Synthesis of XI>

In dehydrated dioxane, 23.11 g (26.1 mmol) of IIIc was dissolved, and concentrated under reduced pressure. The dissolvation and concentration under reduced pressure was repeated three times. The obtained residue was dissolved in 130 mL of dehydrated dioxane, and 226 mg (0.21 mmol) of dimethylaminopyridine, 10.78 g (52.2 mmol) of dicyclohexylcarbodiimide and 5.36 mL (52.2 mmol) of levulinic acid were added and stirred for 2 hours at room temperature. Then, 5 mL of methanol was added to the reaction solution and stirred for 30 minutes. Undissolved substances were removed by filtration and a filtrate was concentrated under reduced pressure, diluted with dichloromethane, and then washed with water. The dichloromethane solution was concentrated under reduced pressure and the obtained residue was purified by medium pressure chromatography (ethylacetate:ethanol=1:0→19:1) to obtain 25.2 g (98%) of a target product XI.

<Synthesis of $XII_1$>

In 38 mL of dehydrated dichloromethane, 17.86 g (15 mmol) of XI was dissolved, and 4.53 mL (28.3 mmol) of triethylsilane and 4.23 mL (28.3 mmol) of diazabicycloundecene were added and stirred for 10 minutes at room temperature. In the reaction mixture, a mixed solution of 2.39 mL (31.1 mmol) of trifluoroacetic acid, 2.74 mL (34.0 mmol) of pyridine and 19 mL of dichloromethane were added to obtain a reaction mixture A.

In acetonitrile, 5.74 g (37.7 mmol) of p-hydroxyphenylacetic acid and 5.21 g (45.3 mmol) of N-hydroxysuccinic acid imide were dissolved, 8.17 g (39.6 mmol) of dicyclohexylcarbodiimide was added under an ice-cooled condition and stirred for 1 hour at 0° C. Undissolved substances were filtrated and a filtrate was added to the reaction mixture A. The reaction mixture was stirred for 1 hour at room temperature. Subsequently, 3.7 mL of piperidine was added thereto and stirred for 30 minutes. The reaction solution was diluted with dichloromethane and washed with water. The dichloromethane solution was concentrated under reduced pressure and the obtained residue was purified by medium pressure chromatography (ethyl acetate:ethanol=19:1→9:1) to obtain 5.03 g (64%) of a target product XII$_Y$.

<Synthesis of XIII>

In 100 mL of dichloromethane, 33.74 g (100 mmol) of FMOC-Suc was dissolved, and 8.25 mL (105 mmol) of 2-(methylamino)ethanol was added under an ice-cooled condition and stirred overnight at room temperature. The reaction solution was washed with water. The dichloromethane solution was concentrated under reduced pressure and the obtained residue was purified by medium pressure chromatography (ethyl acetate:hexan=1:1→1:0) to obtain 28.72 g (97%) of a target product XIII.

<Synthesis of XIV$_Y$>

In dehydrated acetonitrile, 10.38 g (11.6 mmol) of XII$_Y$ was dissolved and concentrated under reduced pressure. The dissolvation and concentration under reduced pressure was repeated three times. In 26 mL of dehydrated acetonitrile, the obtained residue was dissolved and 2.36 mL (29.2 mmol) of pyridine was added to obtain a reaction mixture A.

In 16 mL of dehydrated dichloromethane, 1.38 g (4.64 mmol) of triphosgene was dissolved, and then 1.2 mL (14.6 mmol) of pyridine and 16 mL of a dichloromethane solution of 4.14 g (13.92 mmol) of XIII were added dropwise under an ice-cooled condition. The reaction mixture was stirred for 15 minutes at room temperature. The reaction mixture was added in the reaction mixture A at 0° C. The reaction mixture was stirred for 15 minutes at room temperature. The reaction solution was diluted with dichloromethane and washed with water. The dichloromethane solution was concentrated under reduced pressure and the obtained residue was purified by medium pressure chromatography (ethyl acetate:ethanol=94:6→91:9) to obtain 12.0 g (85%) of a target product XIV$_Y$.

<Synthesis of IV$_Y$>

In 75 mL of pyridine, 9.14 g (7.5 mmol) of XIV$_Y$ was dissolved, 90 mL of a diluted solution (pyridine:acetic acid=2:1) of 3.11 mL (64.3 mmol) of hydrazine 1-hydrate was added and then stirred for 5 minutes at room temperature. Under an ice-cooled condition, 53 mL of acetone was added thereto and stirred for 10 minutes at 0° C., and then diluted with dichloromethane and washed with water. The dichloromethane solution was concentrated under reduced pressure. The obtained residue was purified by medium pressure chromatography (dichloromethane:ethanol=1:0→19:1) to obtain 6.26 g (75%) of a target product IV$_Y$.

<Synthesis of V$_Y$>

In dehydrated acetonitrile and dehydrated dichloromethane, 5.72 g (5.10 mmol) of IV$_Y$ was dissolved, and concentrated under reduced pressure. The dissolvation and concentration under reduced pressure was repeated three times. In 20 mL of dehydrated dichloromethane, the obtained residue was dissolved, and 31 mg (0.26 mmol) of dimethylaminopyridine and 1.01 mL (5.81 mmol) of diisopropylethylamine were added under an ice-cooled condition. Then, 5.1 mL of a methylene chloride solution of 1.25 mL (5.61 mmol) of 2-cyanoethyl diisopropylchlorophosphoroamidite was added dropwise over 5 minutes or more. The mixed solution was stirred for 90 minutes at 0° C. Subsequently, 1.0 mL of methanol was added to the mixed solution and stirred for 15 minutes. The reaction solution was diluted with dichloromethane and washed with water. The dichloromethane solution was concentrated under reduced pressure and the obtained residue was purified by medium pressure chromatography (2% pyridine in ethyl acetate:hexane=2:1-2% pyridine in ethyl acetate 0%→100%, subsequently, 2% pyridine, 20% ethanol 2% pyridine in dichloromethane 1:0→17:3) to obtain 5.72 g (85%) of a target product V$_Y$.

<Confirmation of Structures of Compounds>

The structures of respective compounds (II, IV$_S$, IV$_{S'}$, V$_S$, X, IIIC, XI, XII$_Y$, XIV$_Y$, IV$_Y$, V$_Y$) were confirmed in the following manner. The results are shown in FIGS. 1 to 11C.

[$^1$H-NMR]

Approximately 5 mg of each sample was dissolved in a deuterated solvent, and a $^1$H-NMR spectrum was measured. An internal standard was based on a solvent peak.

[$^{31}$P-NMR]

PPh$_3$ was used as an external standard, and a $^{31}$P-NMR spectrum was measured with −6.2 ppm being a reference value. The measurement was carried out by BCM.

Example 2

Confirmation of Deprotection (V$_Y$)

The protective group of the amidite (V$_Y$) synthesized in Example 1 could be removed under a moderate condition, and a hydroxyl group emerged in a substituent (or a hydroxyl group was exposed on a surface of a substituent) by removing the protective group. These were confirmed by the following process.

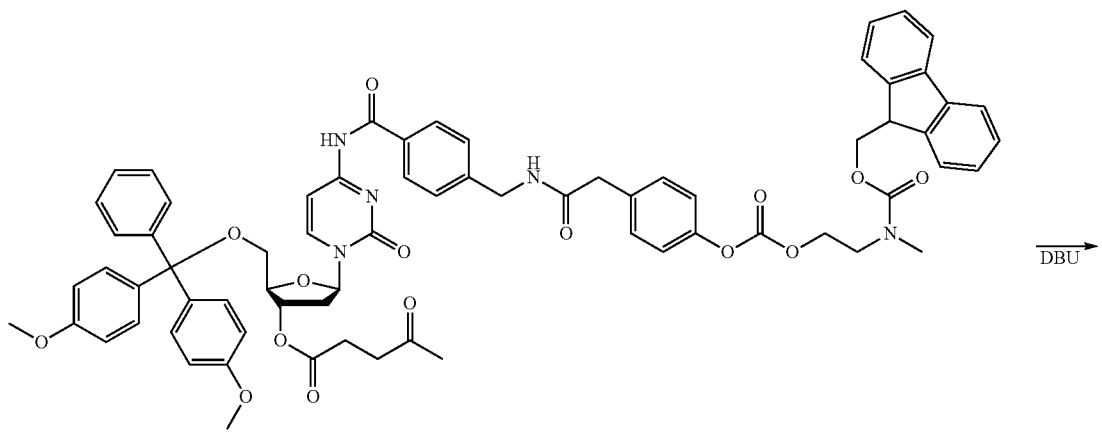

XIV$_{Tyr}$
HPLC chart 1

-continued

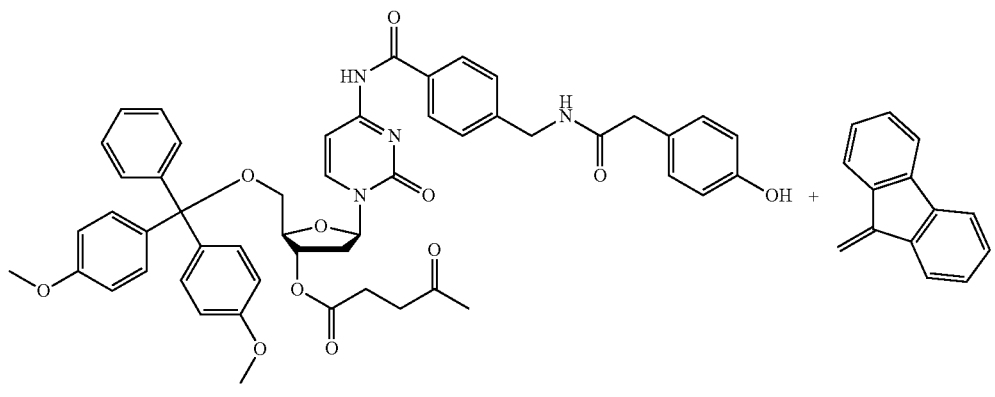

HPLC chart 2

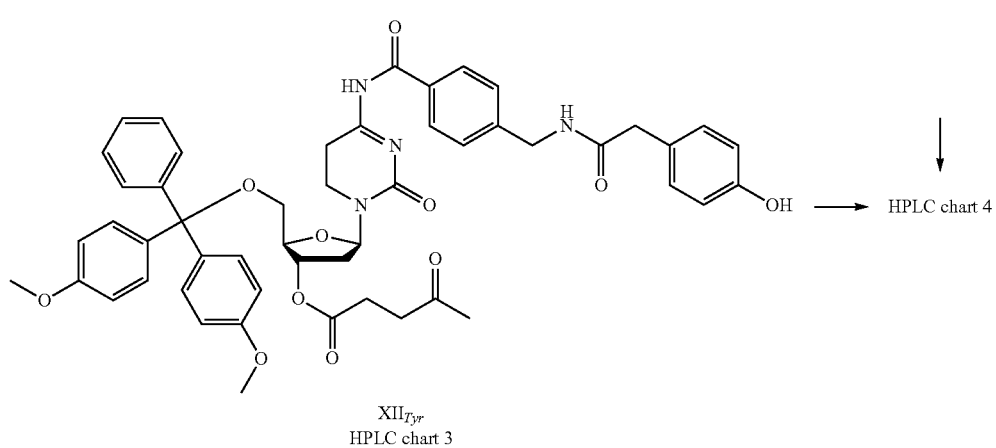

XII$_{Tyr}$
HPLC chart 3
A sample of XIV$_{Tyr}$ treated with DBU and XII$_{Tyr}$ are overlapped.

→ HPLC chart 4

Figure 12:
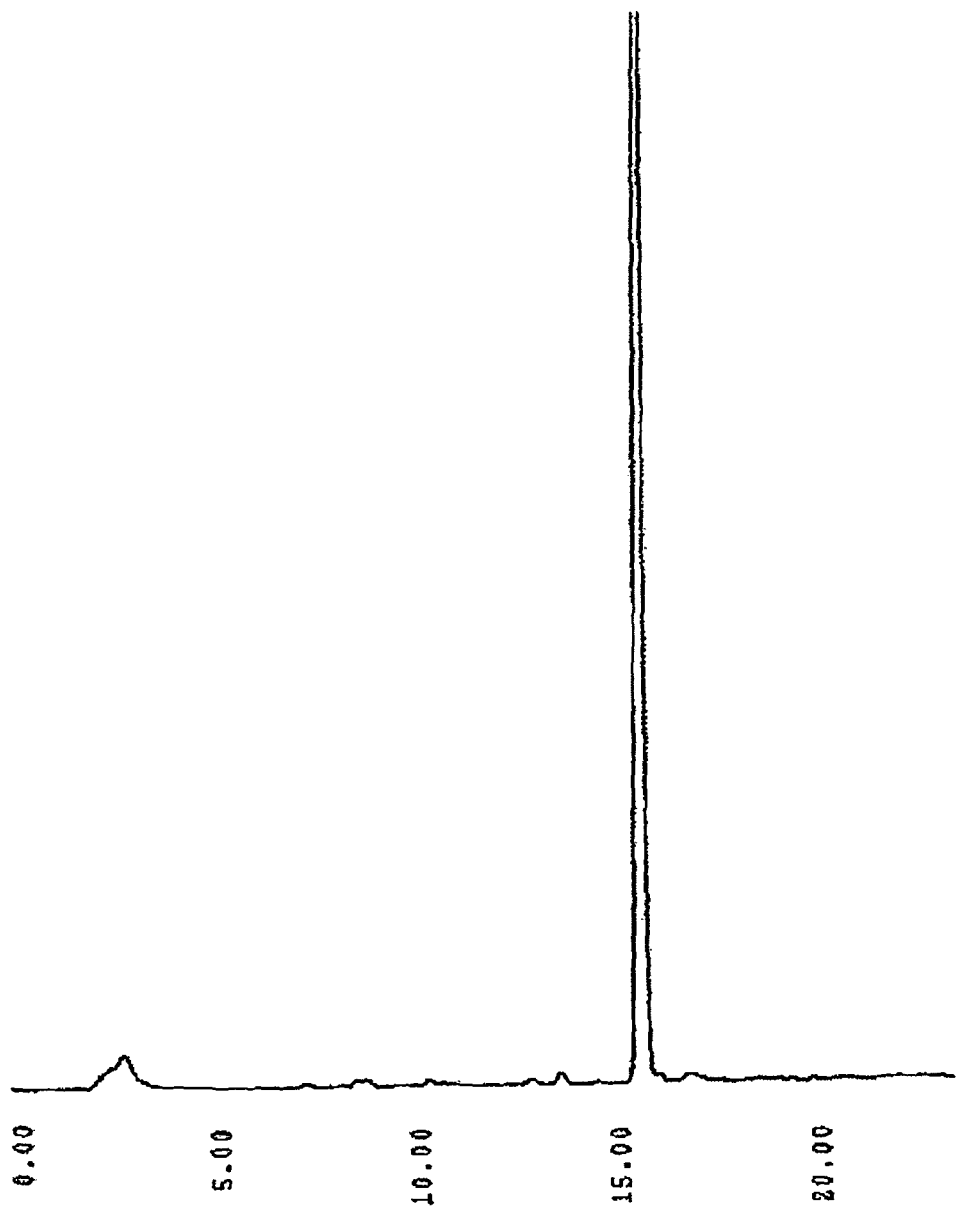
FIG. 12 is a HPLC Chart 1 in Example 2.
Figure 13:
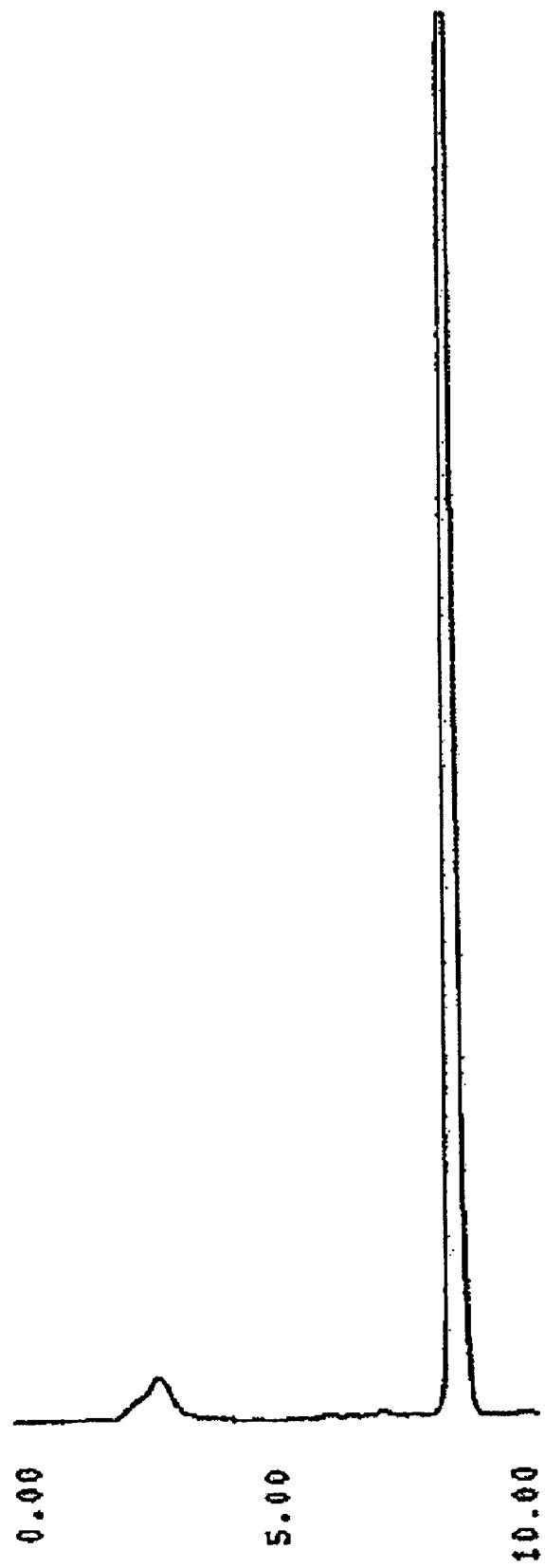
FIG. 13 is a HPLC Chart 2 in Example 2.
Figure 14:
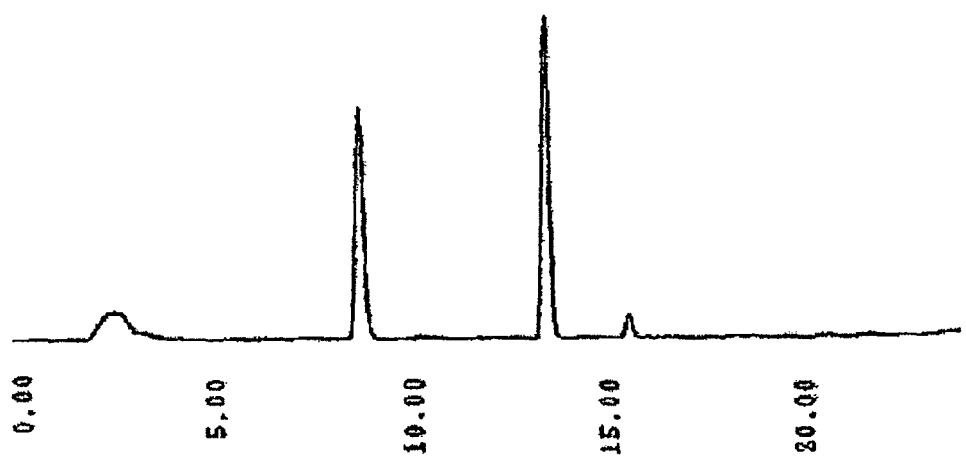
FIG. 14 is a HPLC Chart 3 in Example 2.

First, 1.7 mM of XIV$_Y$ (an intermediate of V$_Y$) having the same substituent and protective group as those in V$_Y$ synthesized in Example 1 (HPLC Chart 1 in FIG. 12), and 10 mM of a DBU (10% DMF, 90% acetonitrile) solution were mixed together and left to stand at room temperature for 15 minutes to obtain a reaction mixture (HPLC Chart 2 in FIG. 13). Moreover, XII$_Y$ synthesized in Example 1, which had the same substituent as that in V$_Y$ but did not have a protective group, was prepared (HPLC Chart 3 in FIG. 14).

Figure 15:
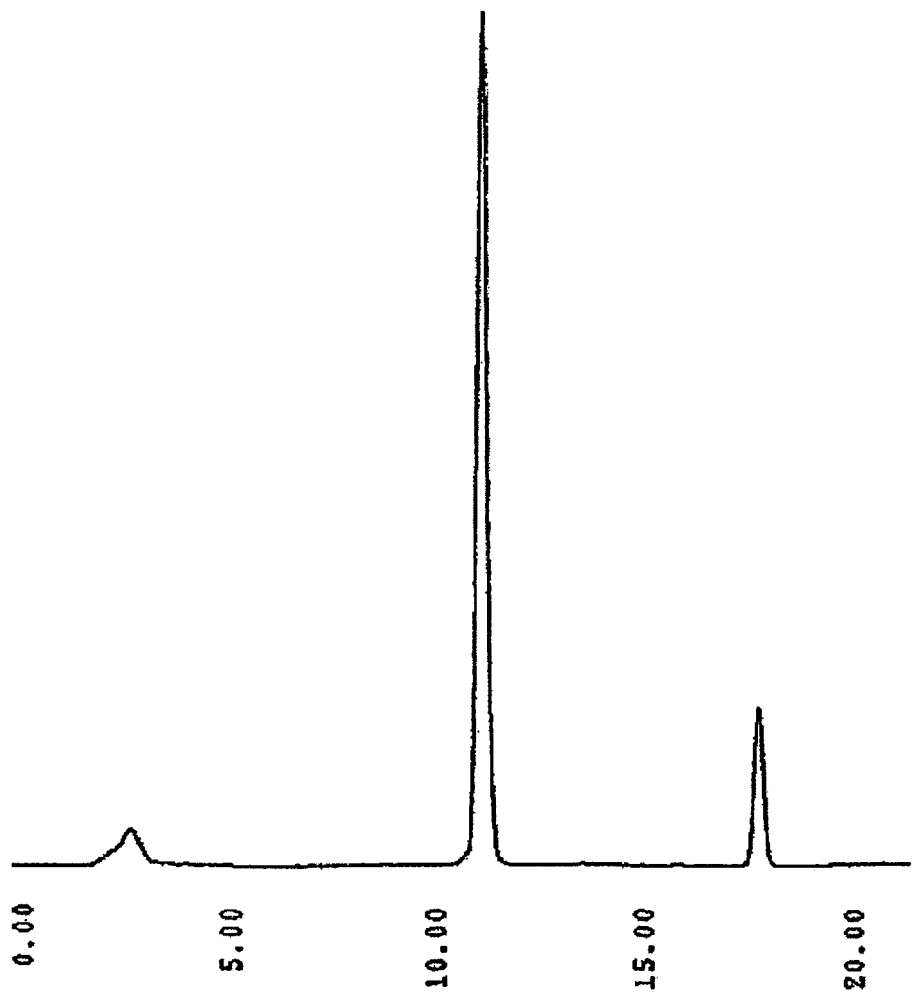
FIG. 15 is a HPLC Chart 4 in Example 2.

Next, a HPLC Chart of the mixture solution of the reaction mixture of HPLC Chart 2 (a sample of XIV$_Y$ treated with DBU) and the compound of HPLC Chart (XII$_Y$) was obtained (HPLC Chart 4 in FIG. 15).

As a result, the reaction mixture of HPLC Chart 2 (the sample of XIV$_Y$ treated with DBU) and the compound of HPLC Chart 3 (XII$_Y$) were identical (HPLC Chart 4 in FIG. 15). Therefore, it was confirmed that, when modified nucleic acid was synthesized using the amidite (V$_Y$) for synthesizing modified nucleic acid, the protective group was removed under a moderate condition such as a DBU treatment in acetonitrile to obtain a desired hydroxyl group-containing modified nucleic acid, in which the protective group was removed and a hydroxyl group emerged (or a hydroxyl group was exposed on a surface thereof).

The HPLC analysis condition in Example 2 was as follows:
[HPLC Analysis Condition]
Flow rate 1 mL/min
A Solution: 100 mM of triethylammonium acetate buffer having pH=7.0
B Solution: acetonitrile
HPLC Charts 1 to 3
B: 50%→80% (0 min→10 min)→100% (→20 min)
HPLC Chart 4
B: 50%→80% (0 min→20 min)

Example 3

Confirmation of Deprotection (V$_S$)

The protective group of the amidite (V$_S$) synthesized in Example 1 could be removed under a moderate condition, and a hydroxyl group emerged in a substituent (or a hydroxyl group was exposed on a surface of a substituent) by removing the protective group. These were confirmed by the following process.

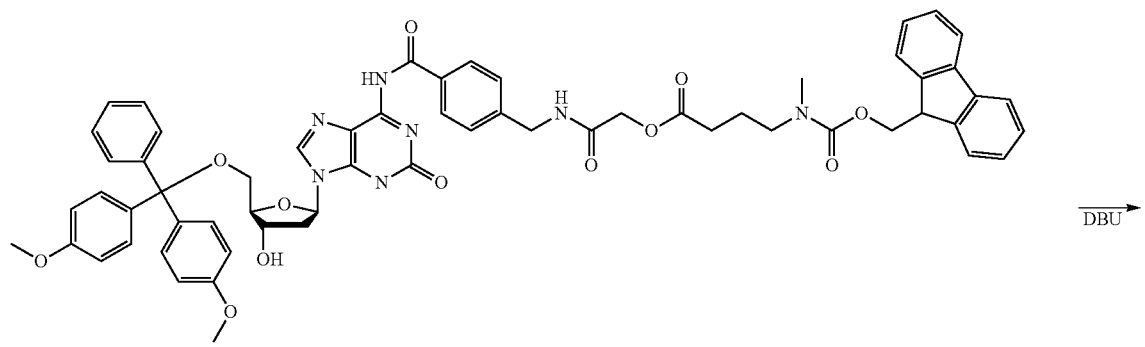

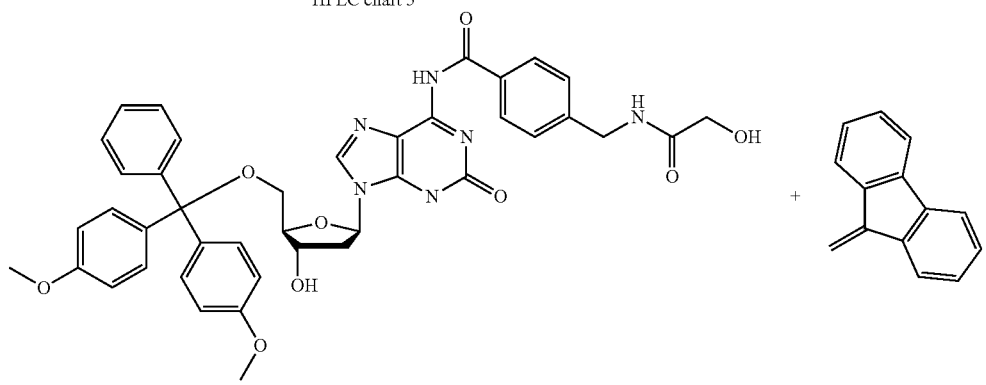

IV$_{Ser}$
HPLC chart 5

HPLC chart 6

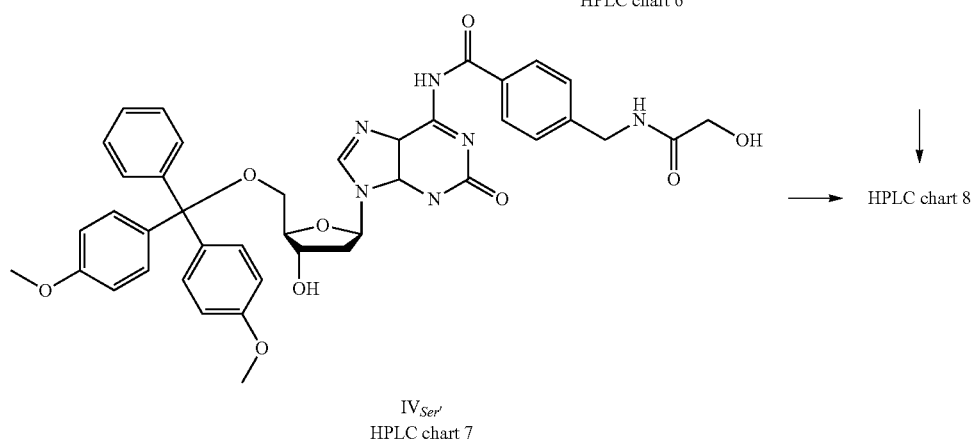

IV$_{Ser'}$
HPLC chart 7

A sample of IV$_{Ser}$ treated with DBU and IV$_{Ser'}$ are overlapped.

Figure 16:
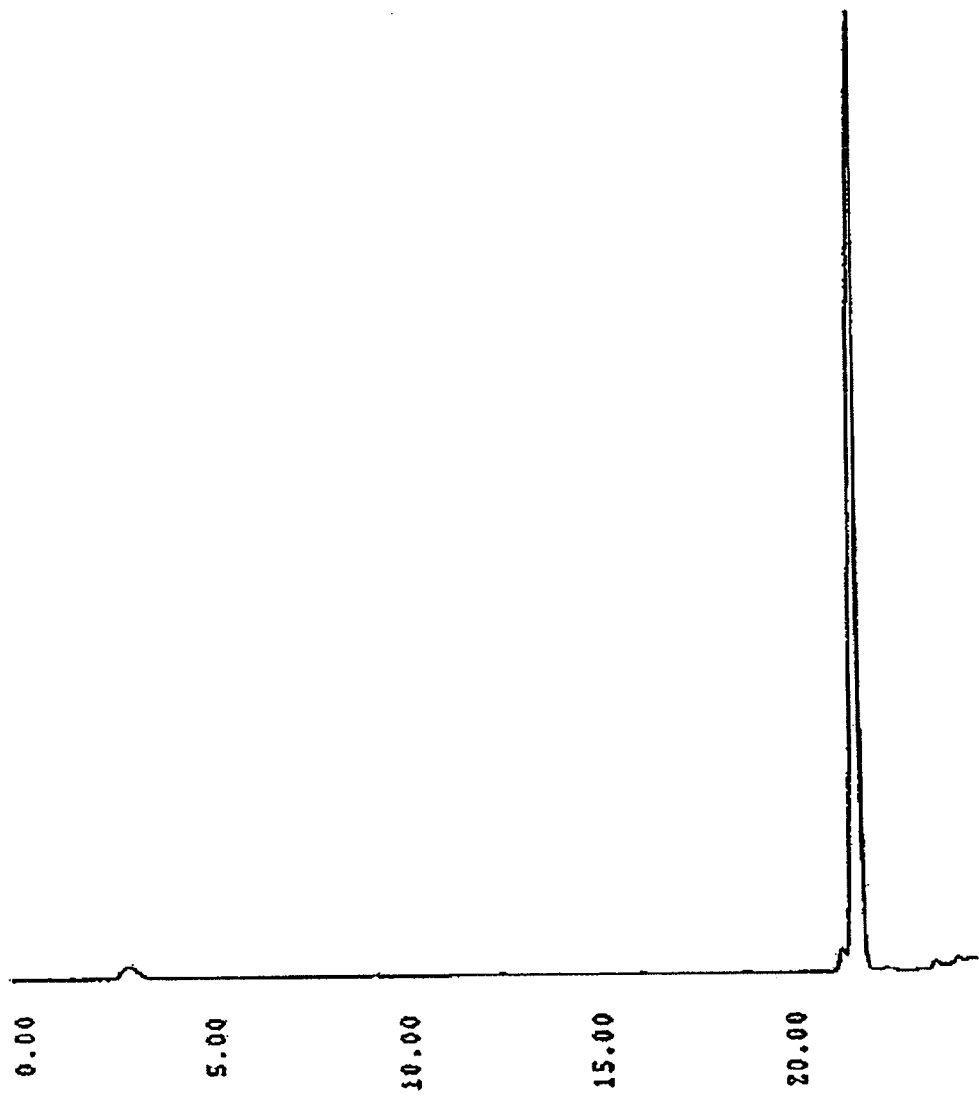
FIG. 16 is a HPLC Chart 5 in Example 3.
Figure 17:
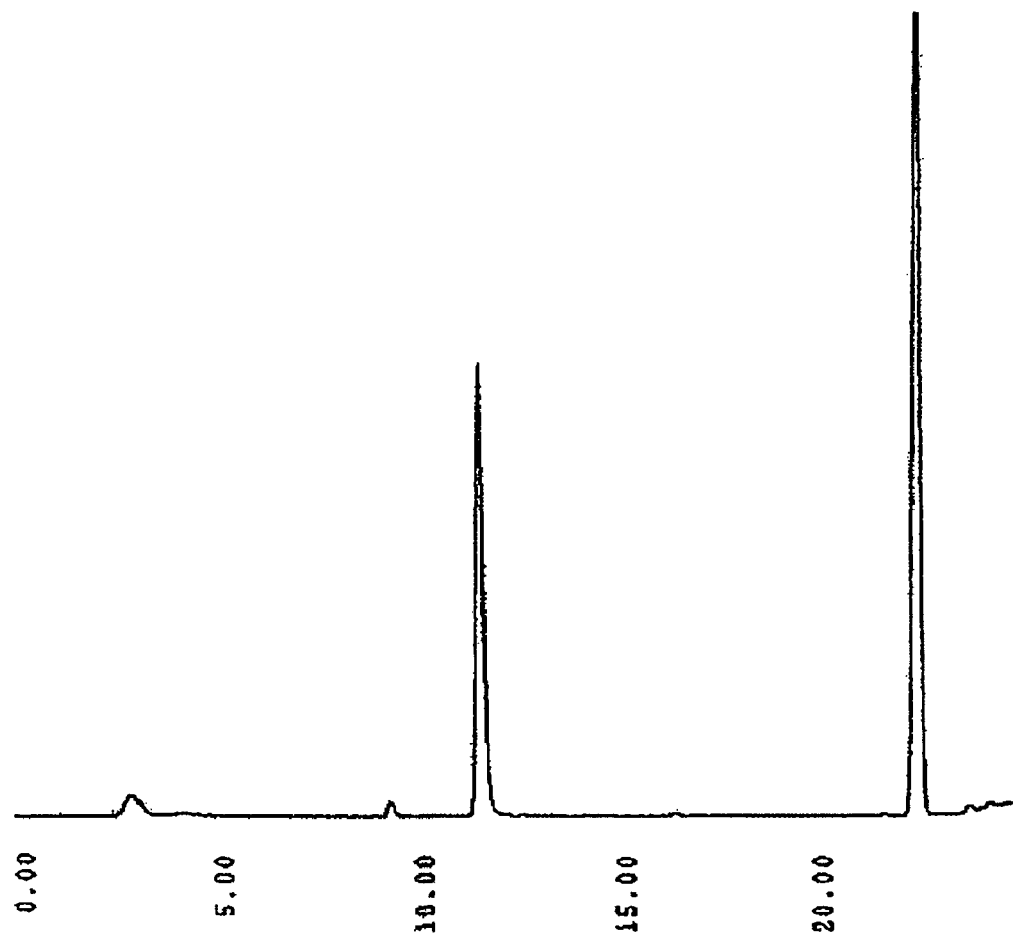
FIG. 17 is a HPLC Chart 6 in Example 3.
Figure 18:
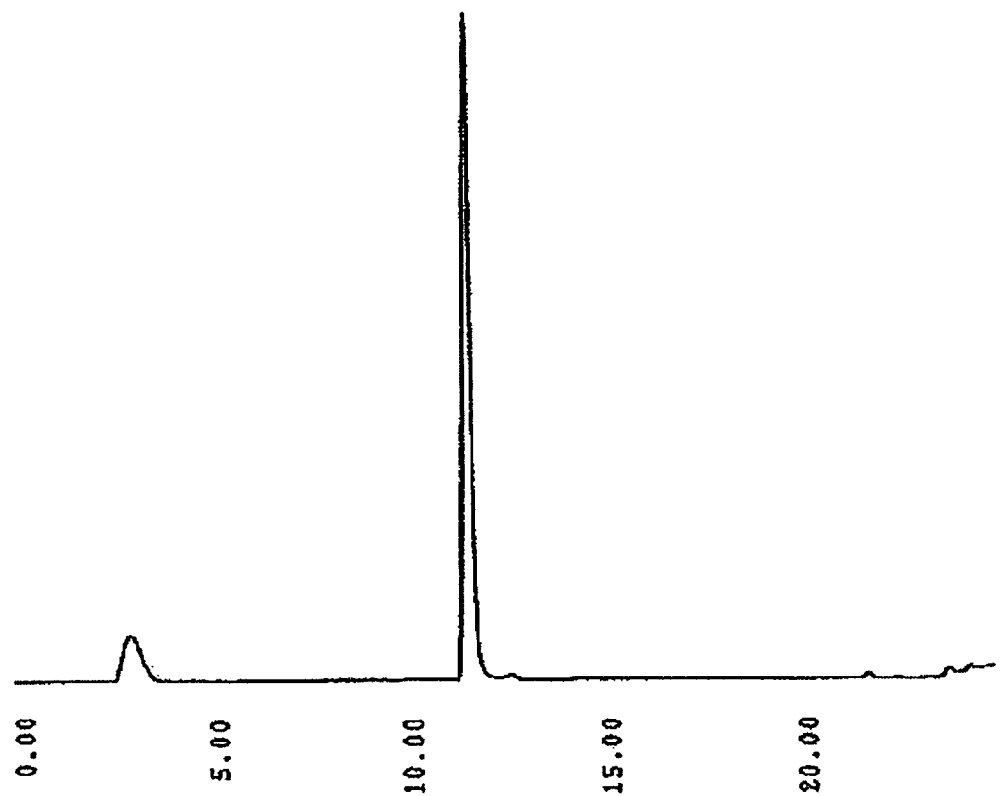
FIG. 18 is a HPLC Chart 7 in Example 3.

First, 0.5 mM of IV$_S$ (an intermediate of V$_S$) V having the same substituent and protective group as those in V$_S$ synthesized in Example 1 (HPLC Chart 5 in FIG. 16), and 10 mM of a DBU (10% DMF, 90% acetonitrile) solution were loaded together and left to stand at room temperature for 15 minutes to obtain a reaction mixture (HPLC Chart 6 in FIG. 17). Moreover, IV$_{S'}$ synthesized in Example 1, which had the same substituent as that in V$_S$ but did not have a protective group, was prepared (HPLC Chart 7 in FIG. 18).

Figure 19:
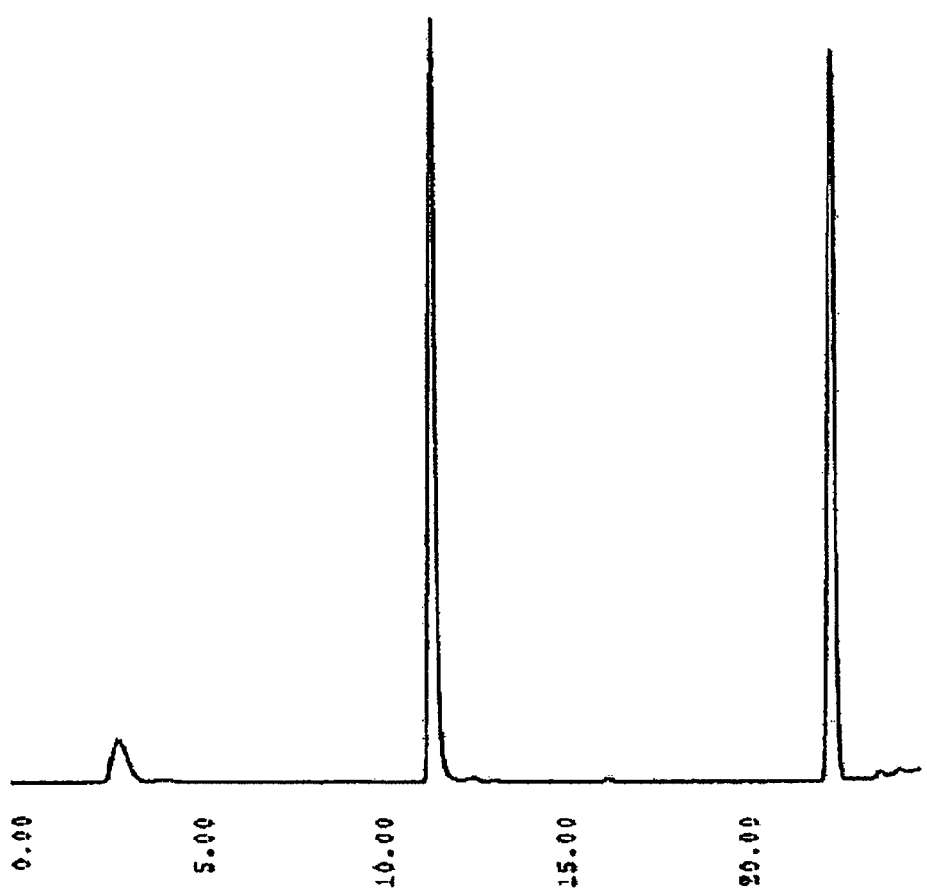
FIG. 19 is a HPLC Chart 8 in Example 3.

Next, a HPLC Chart of the mixture solution of the reaction mixture of HPLC Chart 6 (a sample of IV$_S$ treated with DBU) and the compound of HPLC Chart 7 (IV$_{S'}$) was obtained (HPLC Chart 8 in FIG. 19).

Figure 20:
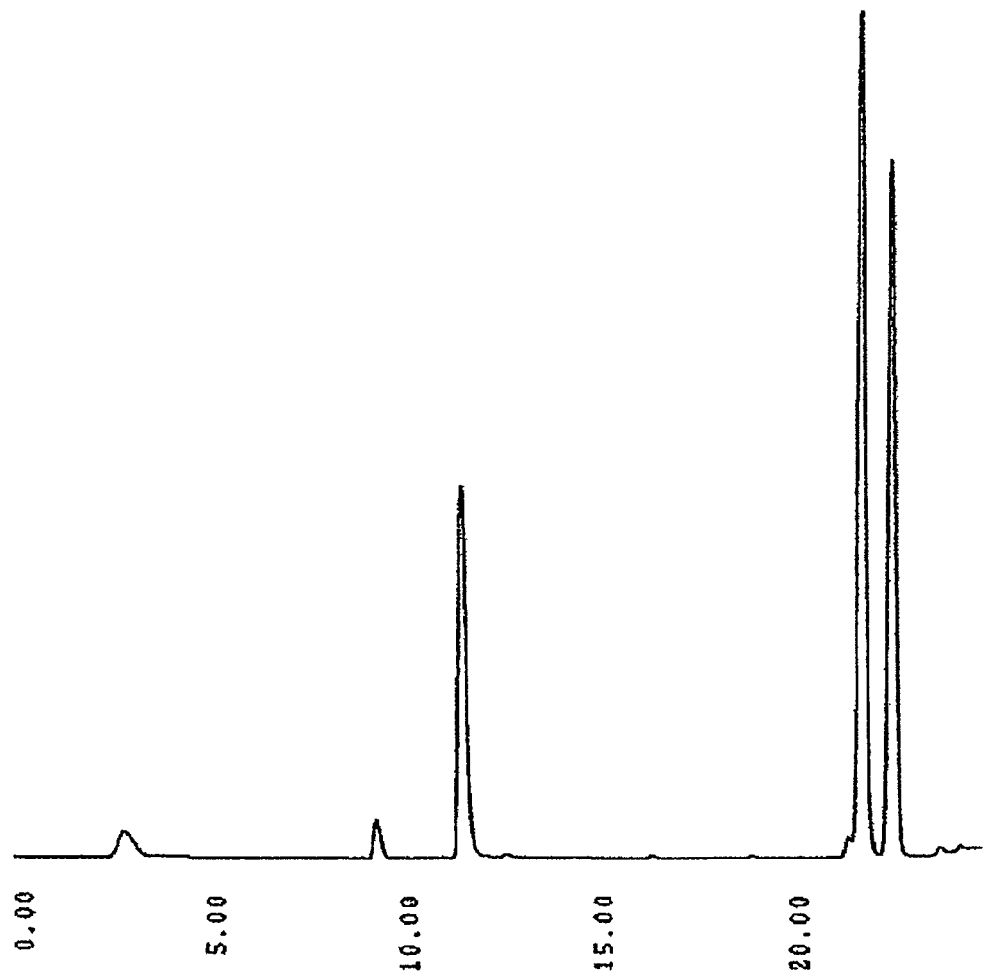
FIG. 20 is a HPLC Chart 9 in Example 3.

Moreover, as references, a HPLC Chart of the mixture solution of IV$_S$ and a sample formed by neutralizing the reaction mixture of HPLC Chart 6 (the sample of IV$_S$ treated with DBU) with acetic acid was obtained (HPLC Chart 9 in FIG. 20).

As a result, the reaction mixture of HPLC Chart 6 (the sample of IV$_S$ treated with DBU) and the compound of HPLC Chart 7 (IV$_{S'}$) were identical (HPLC Chart 8). Therefore, it was confirmed that, when modified nucleic acid was synthesized using the amidite (V$_S$) for synthesizing modified nucleic acid, the protective group was removed under a moderate condition such as a DBU treatment in acetonitrile to obtain a desired hydroxyl group-containing modified nucleic acid, in which the protective group was removed and a hydroxyl group emerged (or a hydroxyl group was exposed on a surface thereof).

Moreover, from the result of HPLC Chart 9 (the sample formed by neutralizing the sample of $IV_S$ treated with DBU and $IV_S$ were overlapped), it was confirmed that a hydrophobic product obtained by DBU treatment was different from $IV_S$, that is, $IV_S$ was completely eliminated by DBU treatment.

The HPLC analysis condition in Example 3 was as follows:

[HPLC Analysis Condition]

Flow rate 1 mL/min

A Solution: 100 mM of triethylammonium acetate buffer having pH=7.0

B Solution: acetonitrile

HPLC Charts 4 to 9

B: 30%→80% (0 min→20 min)

Figure 21A:
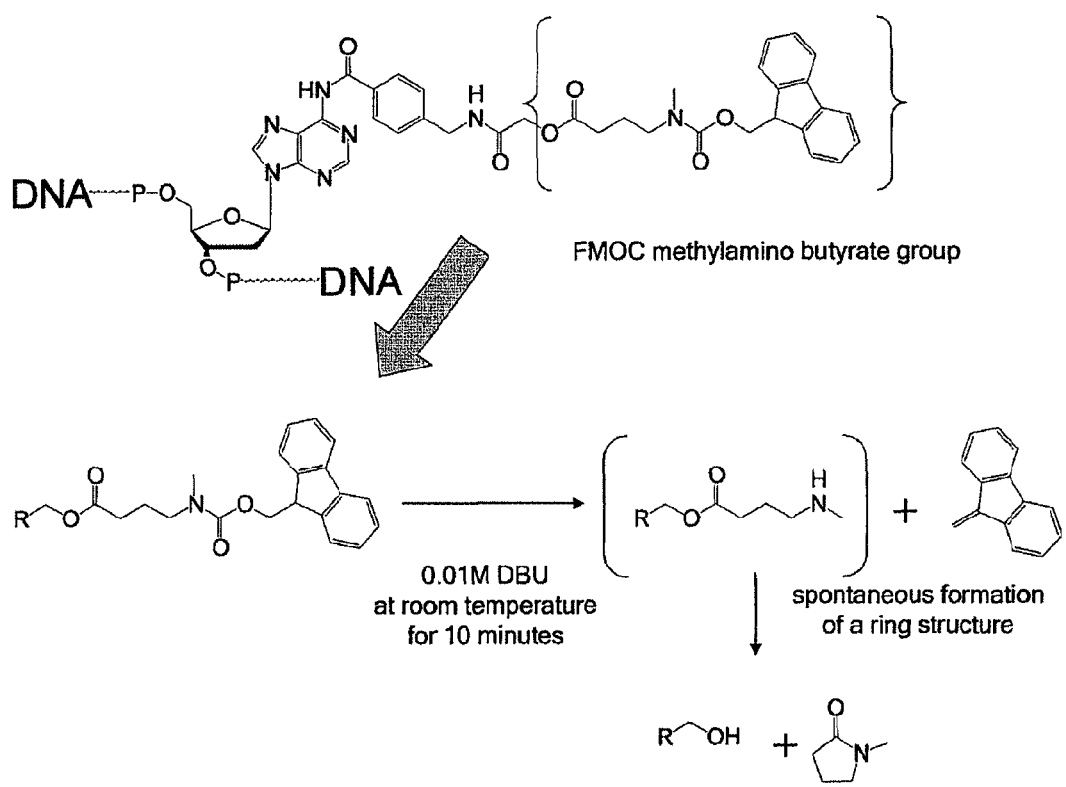
FIG. 21A shows an example of a mechanism by which a protective group in an amidite (V$_S$) for synthesizing modified nucleic acid is removed.
Figure 21B:
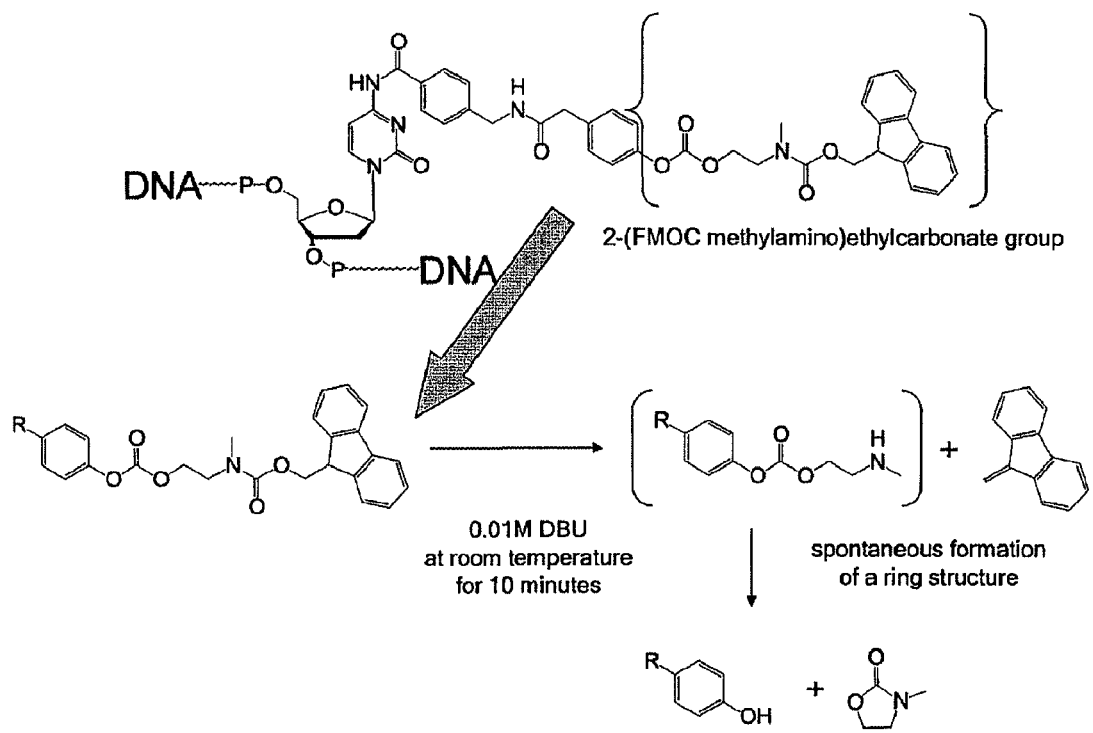
FIG. 21B shows an example of a mechanism by which a protective group in an amidite (V$_Y$) for synthesizing modified nucleic acid is removed.

As a mechanism of producing a desired hydroxyl group-containing modified nucleic acid in which a hydroxyl group emerges (or a hydroxyl group is exposed on a surface thereof), by removing a protective group of the amidite for synthesizing modified nucleic acid under a moderate condition such as DBU treatment in acetonitrile, for example, a mechanism as shown in FIGS. 21A and 21B can be presumed. That is, by means of DBU treatment in acetonitrile, first, a fluorenyl group is removed from the protective group, subsequently, an emerged amine (amine exposed on the surface thereof) attacks a carbonyl group or carbonate group so as to spontaneously form a ring, and then the protective group is completely removed. Therefore, a hydroxyl group emerges in the substituent (or a hydroxyl group is exposed on a surface of the substituent) to produce a hydroxyl group-containing modified nucleic acid (or modified nucleic acid) (FIGS. 21A and 21B).

According to an amidite for synthesizing modified nucleic acid and a method for synthesizing modified nucleic acid, a hydroxyl group-containing modified nucleic acid can be effectively obtained. The obtained modified nucleic acid can be bonded to a target substance such as a protein via a hydroxyl group. Therefore, the modified nucleic acid can be preferably used, for example, for analysis of a target substance such as a protein.

What is claimed is:

1. A method for synthesizing a modified DNA by a treatment of a modified solid support to which a nucleotide or a nucleoside is added comprising:

(i) repeating a series of the following sequential steps (a) to (d) which is conducted in order of (a), (b), (c) and (d) or in order of (a), (c), (b) and (d) and which results in an addition of one nucleotide to the modified solid support until a sequence of a final modified DNA is obtained:

(a) coupling a selected amidite having a 5'-hydroxyl protective group to a 5'-hydroxyl group of a nucleoside or a nucleotide on the modified solid support to form a phosphite triester linkage between the nucleoside structure in the selected amidite and the nucleoside or the nucleotide on the modified solid support;

(b) optionally blocking unreacted hydroxyl groups of the nucleoside or the nucleotide on the modified solid support;

(c) oxidizing the phosphite triester linkage to form a phosphotriester linkage;

(d) removing the 5'-hydroxyl protective group derived from the selected amidite to generate a 5'-hydroxyl group for coupling a subsequent amidite as a selected amidite in subsequent (a); and (ii) removing the final modified DNA from the solid support;

wherein the selected amidites applied in (a) to (d) include at least one or more amidites having the General Formula (I);

wherein the modified DNA obtained is converted into an unmodified DNA from which—Y—Z of the amidite having the General Formula (I) has been removed in concentrated ammonia water from X of the amidite having the General Formula (I):

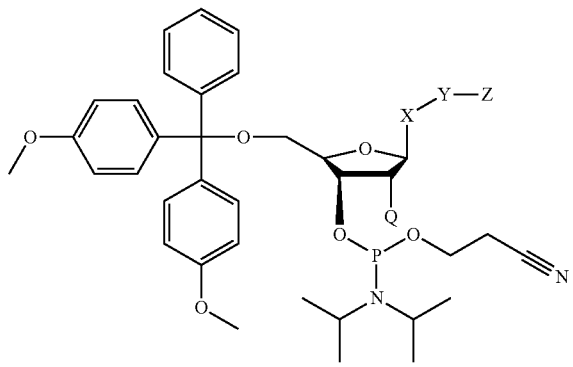

General Formula (I)

wherein X represents a base selected from the group consisting of 9-adeninyl, 9-guaninyl and 1-cytosinyl, wherein Y is represented by the General Formula (IV) or the General Formula (V):

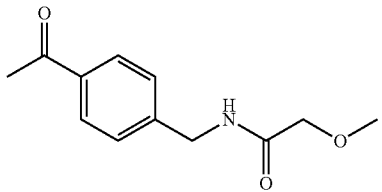

General Formula (IV)

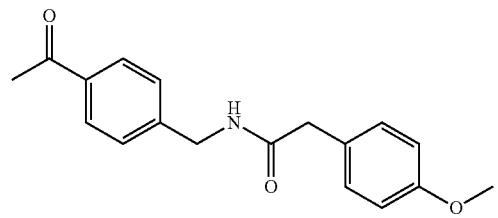

General Formula (V)

wherein Z is represented by the General Formula (II) or the General Formula (III):

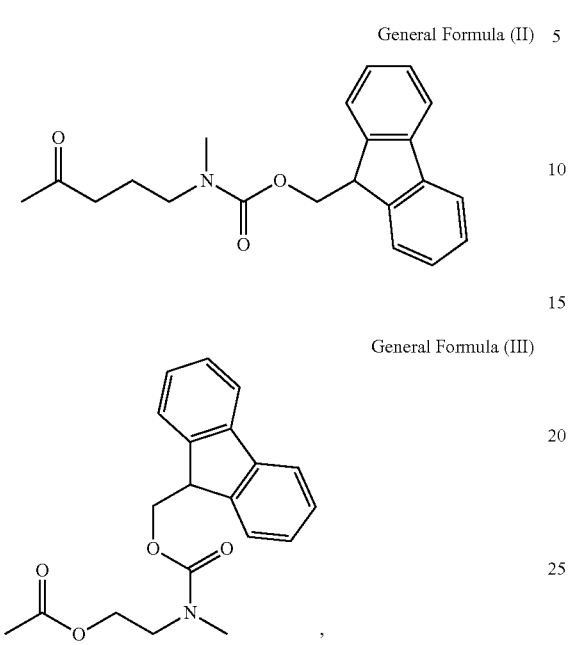

General Formula (II)

General Formula (III)

wherein Q represents a substituent selected from the group consisting of a hydrogen atom, a hydroxyl group and a hydroxyl group protected by a protective group, and wherein Y bonds to an amino group of X that is located at position 2 of 9-adeninyl, at position 2 of 9-guaninyl or at position 4 of 1-cytosinyl.

2. The method according to claim 1, further comprising, after the sequence of the final modified DNA is obtained on the solid support, removing Z from Y while the bond between X and Y is maintained in the General Formula (I) with a base selected from the group consisting of 1,8-diazabicyclo [5.4.0] undec-7-ene (DBU), 1,5-diazabicyclo[4.3.0]-5-nonene (DBN) and tetramethylguanidine in the aprotic solvent.

3. The method according to claim 2, wherein Z is removed from the modified DNA by cleavage of the Y—Z bond with a base selected from the group consisting of 1,8-diazabicyclo[5.4.0]undec-7-ene (DBU), 1,5-diazabicyclo[4.3.0]-5-nonene (DBN) and tetramethylguanidine in the aprotic solvent, and wherein a terminal of Y to which Z has been bond becomes the 5'-hydroxyl group by the removal of Z.

4. The method according to claim 1, further comprising, after the sequence of the final modified DNA is obtained on the solid support, removing Z from Y while the bond between X and Y is maintained in the General Formula (I) with 1,8-diazabicyclo[5.4.0]undec-7-ene (DBU) at a concentration of 0.01M or less in the aprotic solvent.

5. The method according to claim 1, further comprising removing Z from Y within 15 minutes, while the bond between X and Y is maintained in the General Formula (I).

6. The method according to claim 1, wherein the modified DNA is synthesized with an automatic nucleic acid synthesizer.

7. The method according to claim 1, wherein the selected amidites in (a) to (d) further comprise at least one or more amidites having the General Formula (VI):

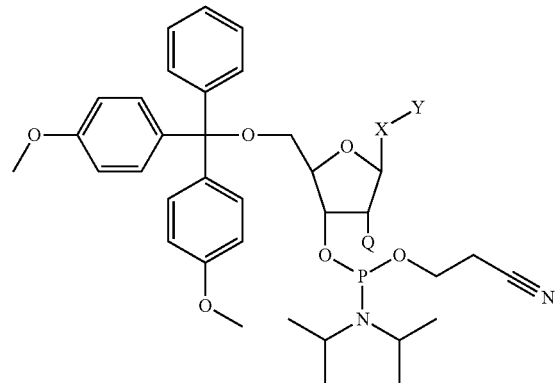

General Formula (VI)

wherein in the General Formula (VI), X represents a base, wherein in the General Formula (VI), Y represents a protective group derived from a 4-aminobutyric acid derivative, an o-aminomethylbenzoic acid derivative, an o-aminophenylacetic acid derivative, an o-aminoethylbenzoic acid derivative, an o-aminomethylphenylacetic acid derivative, an o-aminophenylpropionic acid derivative, or a 5-aminovaleric acid derivative; and wherein in the General Formula (VI), Q represents a hydrogen atom or a hydroxy group.

8. A modified DNA, obtained by a method for synthesizing the modified DNA by a treatment of a modified solid support to which a nucleotide or a nucleoside is added comprising:

(i) repeating a series of the following sequential steps (a) to (d) which is conducted in order of (a), (b), (c) and (d) or in order of (a), (c), (b) and (d) and which results in an addition of one nucleotide to the modified solid support until a sequence of a final modified DNA is obtained:

(a) coupling a selected amidite having a 5'-hydroxyl protective group to a 5'-hydroxyl group of a nucleoside or the nucleotide on the modified solid support to form a phosphite triester linkage between the nucleoside structure in the selected amidite and the nucleoside or the nucleotide on the modified solid support;

(b) optionally blocking unreacted hydroxyl groups of the nucleoside or the nucleotide on the modified solid support;

(c) oxidizing the phosphite triester linkage to form a phosphotriester linkage;

(d) removing the 5'-hydroxyl protective group derived from the selected amidite to generate a 5'-hydroxyl group for coupling a subsequent amidite as a selected amidite in subsequent (a); and (ii) removing the final modified DNA from the solid support;

wherein the selected amidites in (a) to (d) include at least one or more amidites selected from the group consisting of an amidite having the Structural Formula (1') and an amidite having the Structural Formula (2');

wherein the modified DNA obtained is converted into an unmodified DNA from which at least one modified group that bonds to an amino group of at least one base derived from the amidite having the Structural Formula (1') or the Structural Formula (2') has been removed in concentrated ammonia water;

Structural Formula (1')

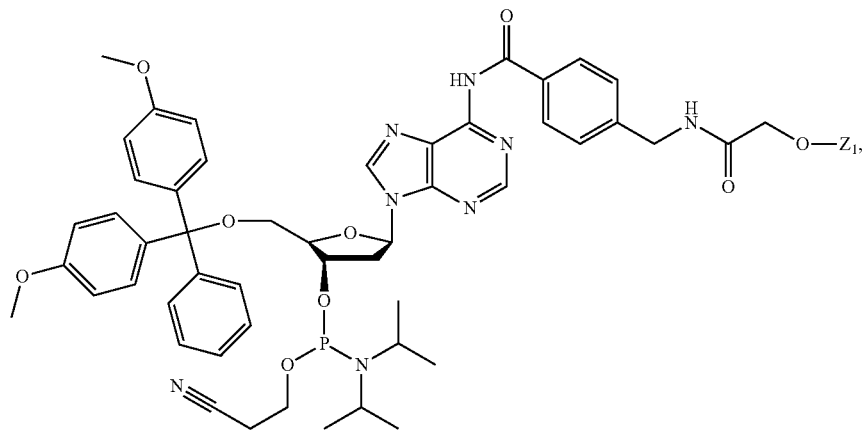

General Formula (II')

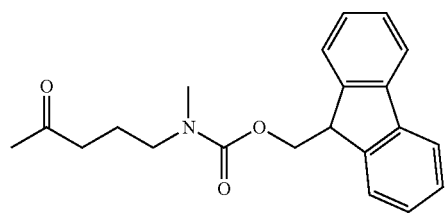

General Formula (II')

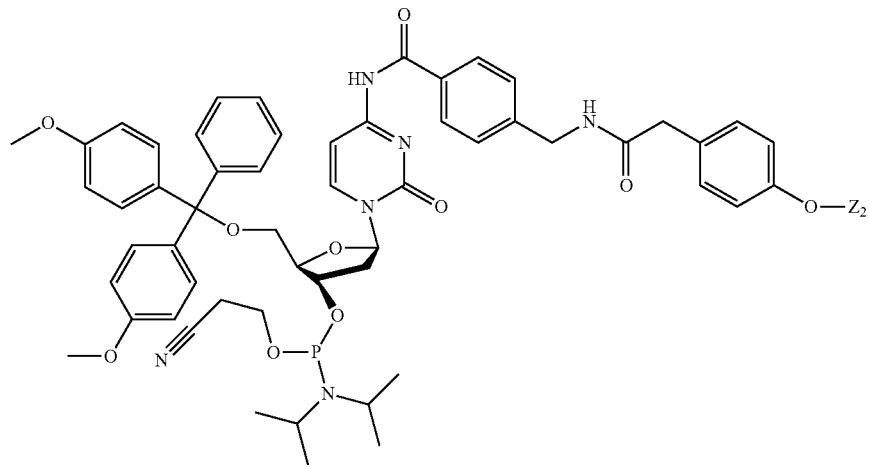

Structural Formula (2'), and wherein $Z_2$ represents General Formula (III'):

General Formula (III')

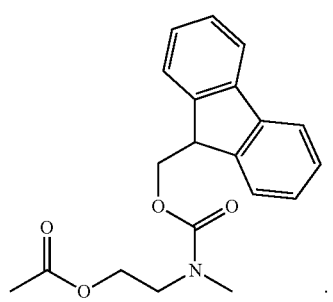

9. The modified DNA according to claim 8, wherein the method for synthesizing the modified DNA further comprises removing $Z_1$ of the Structural Formula (1') or $Z_2$ of the Structural Formula (2') with 1,8-diazabicyclo[5.4.0]undec-7-ene in the aprotic solvent.

10. The method according to claim 1, wherein the aprotic solvent is at least one selected from the group consisting of acetonitrile, dichloromethane, DMF and N-methylpyrrolidone.

11. The modified DNA according to claim 8, wherein the selected amidites in (a) to (d) further comprise at least one or more amidites having the General Formula (VI):

General Formula (VI)

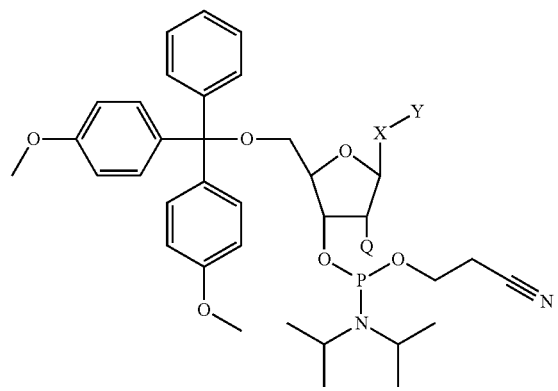

wherein in the General Formula (VI), X represents a base, wherein in the General Formula (VI), Y represents a protective group derived from a 4-aminobutyric acid derivative, an o-aminomethylbenzoic acid derivative, an o-aminophenylacetic acid derivative, an o-aminoethylbenzoic acid derivative, an o-aminomethylphenylacetic acid derivative, an o-aminophenylpropionic acid derivative, or a 5-aminovaleric acid derivative; and wherein in the General Formula (VI), Q represents a hydrogen atom or a hydroxy group.

* * * * *